US008333996B2

(12) United States Patent
Lee et al.

(10) Patent No.: US 8,333,996 B2
(45) Date of Patent: *Dec. 18, 2012

(54) CALCIUM PHOSPHATE DELIVERY VEHICLE AND ADJUVANT

(75) Inventors: D. Duke Lee, Brookline, MA (US); Maria Aiolova, Brookline, MA (US)

(73) Assignee: Etex Corporation, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/153,133

(22) Filed: Sep. 15, 1998

(65) Prior Publication Data

US 2003/0082232 A1 May 1, 2003

Related U.S. Application Data

(63) Continuation-in-part of application No. 08/729,342, filed on Oct. 16, 1996, now Pat. No. 6,541,037.

(51) Int. Cl.
A01N 59/26 (2006.01)
A61K 33/42 (2006.01)
A61K 51/00 (2006.01)
A61M 36/14 (2006.01)

(52) U.S. Cl. ...................... 424/602; 424/1.57
(58) Field of Classification Search .................. 424/484, 424/130.1, 184.1, 489, 491, 278.1, 602, 603, 424/278; 514/769

See application file for complete search history.

(56) References Cited

U.S. PATENT DOCUMENTS

| | | | |
|---|---|---|---|
| 2,967,802 A | 1/1961 | Towey et al. | |
| 3,608,071 A | 9/1971 | Relyveld et al. | |
| 3,925,545 A | 12/1975 | Relyveld | |
| 4,016,252 A | 4/1977 | Relyveld | |
| 4,110,432 A * | 8/1978 | Wilkinson et al. | 424/85 |
| 4,329,332 A | 5/1982 | Couvreur et al. | |
| 5,085,861 A * | 2/1992 | Gerhart et al. | 424/78.17 |
| 5,284,655 A * | 2/1994 | Bogdansky et al. | 424/422 |
| 5,324,519 A * | 6/1994 | Dunn et al. | 424/426 |
| 5,443,832 A * | 8/1995 | Amerongen | 424/278 |
| 5,462,751 A * | 10/1995 | Kossovsky et al. | 424/494 |
| 5,508,342 A * | 4/1996 | Antonucci et al. | 524/788 |
| 5,650,176 A | 7/1997 | Lee et al. | 424/602 |
| 5,676,976 A | 10/1997 | Lee et al. | |
| 5,683,461 A | 11/1997 | Lee et al. | 623/16 |
| 5,723,283 A * | 3/1998 | Classen | 435/4 |
| 5,782,971 A * | 7/1998 | Constantz et al. | 106/690 |
| 5,968,253 A * | 10/1999 | Poser et al. | 106/691 |
| 6,027,742 A | 2/2000 | Lee et al. | 424/422 |
| 6,117,456 A | 9/2000 | Lee et al. | 424/602 |
| 6,132,463 A | 10/2000 | Lee et al. | 623/16 |
| 6,139,578 A | 10/2000 | Lee et al. | 623/16.11 |
| 6,214,368 B1 * | 4/2001 | Lee et al. | 424/423 |
| 6,277,151 B1 | 8/2001 | Lee et al. | 623/23.61 |
| 6,287,341 B1 | 9/2001 | Lee et al. | 623/16.11 |
| 6,331,312 B1 | 12/2001 | Lee et al. | 424/426 |
| 6,541,037 B1 * | 4/2003 | Lee et al. | 424/602 |

FOREIGN PATENT DOCUMENTS

WO WO 98/16209 4/1998

OTHER PUBLICATIONS

Gupta et al., "Adjuvant Properties of Aluminum and Calcium Compounds," *Vaccine Design* Chapter 8 pp. 229-248 (1995).
Gupta et al., "Comparison of Adjuvant Activities of Aluminium Phosphate, Calcium Phosphate and Stearyl Tyrosine for Tetanus Toxoid," *Biologicals* 22:53-63 (1994).
Ickovic et al., "Calcium-Phosphate-Adjuvanted Allergens: Total and Specific IgE Levels Before and After Immunotherapy with House Dust and *Dermatophagoides pteronyssinus* Extracts," *Ann. Immunol.* 134D:358-398 (1983).
Kato et al., "Relationship Between Hemolytic Activity and Adsorption Capacity of Aluminum Hydroxide and Calcium Phosphate as Immunological Adjuvants for Biologicals," *Microbiol. Immunol.* 38:543-548 (1994).
Kreuter et al., "Influence of the Particle Size on the Adjuvant Effect of Particulate Polymeric Adjuvants," *Vaccine* 4:125-129 (1986).
Relyveld, "Preparation and Use of Calcium Phosphate Adsorbed Vaccines," *Develop. biol. Standard*, 65:131-136 (1986).
Relyveld et al., "Calcium Phosphate Adjuvanted Allergens," *Annals of Allergy* 54:521-529 (1985).
Relyveld, "Current Developments in Production and Testing of Tetanus and Diphtheria Vaccines," *New Developments with Human and Veterinary Vaccines* pp. 51-76 (1980).
Relyveld et al., "Humoral Response in Rabbits Immunized with Calcium Phosphate Adjuvanted HIV-1 gp160 Antigen," *Biomed & Pharmacother* 48:79-83 (1994).
Vassilev, "Aluminium Phosphate but Not Calcium Phosphate Stimulates the Specific IgE Response in Guinea Pigs to Tetanus Toxoid," *Allergy* 33:155-159 (1978).
Aggerbeck and Heron, "Adjuvanticity of Aluminum Hydroxide and Calcium Phosphate in Diphtheria-Tetanus Vaccines" *Vaccine* 13:1360-1365 (1995) [Abstract Only].
Goto et al., "Local Tissue Irritating Effects and Adjuvant Activities of Calcium Phosphate and Aluminum Hydroxide with Different Physical Properties" *Vaccine* 15:1364-1371 (1997).
Goto et al., "Studies on the Toxicities of Aluminum Hydroxide and Calcium Phosphate as Immunological Adjuvants for Vaccines" *Vaccine* 11:914-918 (1993).
Gupta et al., "Adjuvants—A Balance Between Toxicity and Adjuvanticity" *Vaccine* 11:293-306 (1993).
Kossovsky et al., "Preservation of Surface-Dependent Properties of Viral Antigens Following Immobilization on Particulate Ceramic Delivery Vehicles" *Journal of Biomedical Materials Research* 29:561-573 (1995).

(Continued)

*Primary Examiner* — Sreeni Padmanabhan
*Assistant Examiner* — Layla Soroush
(74) *Attorney, Agent, or Firm* — Clark & Elbing LLP; Todd Armstrong

(57) ABSTRACT

An improved calcium phosphate delivery vehicle or adjuvant with incorporated adjuvanticity enhancing means and methods of producing same are disclosed. The adjuvant can be fabricated to desired formulations as appropriate and based on the intended purpose. Particle sizes can be adjusted to enhance adjuvant activity. Other supplemental materials may be added as desired and in appropriate proportions to selectively elicit preferred components of the immune system and to enhance the adjuvant's effect on the host response.

9 Claims, No Drawings

OTHER PUBLICATIONS

Kossovsky et al., "Surface-Modified Nanocrystalline Ceramics for Drug Delivery Applications" *Biomaterials* 15:1201-1207 (1994).

Atkinson and Grant, "Pressure Changes in Polymerizing Polymethyl Methacrylate," *J. Dent. Res.* 44:1040-1044, 1965.

BASF Corporation, "Arcylic Acid: A Summary of Safety and Handling," 3rd Edition, 2002.

Combes et al., "Calcium Carbonate-Calcium Phosphate Mixed Cement Compositions for Bone Reconstruction," *Journal of Biomedical Materials Research*, Part A, 7:318-328, 2006.

Dorozhkin, "Calcium Orthophosphate Cements and Concretes," *Materials* 2:221-291, 2009.

Knets et al., "Stiffness and Strength of Composite Acrylic Bone Cements," *J. Achieve. Mater. Manuf. Eng.* 20:135-138, 2006.

Rohm and Haas Technical Bulletin on "Monomers: Safe Handling," Jul. 7, 2006.

Saltzman et al., "Total Ankle Replacement Revisited," *J. Ortho. Sports Phys. Ther.* 30:56-67, 2000.

\* cited by examiner

CALCIUM PHOSPHATE DELIVERY VEHICLE AND ADJUVANT

This application is a continuation-in-part of U.S. Ser. No. 08/729,342 filed Oct. 16, 1996, now U.S. Pat. No. 6,541,037, which is incorporated by reference in its entirety.

FIELD OF THE INVENTION

The present invention relates to improved calcium phosphate vaccine delivery vehicles, adjuvants, and methods for producing the same.

DESCRIPTION OF THE NEAREST ART

An ideal vaccine delivery system should be designed to introduce an immunogen to a desired site of action and release it at an appropriate and controllable rate. The carrier should also be non-toxic and should not remain in the host after its use. Both the adjuvant and immunogen should be pharmaceutically stable and the delivery system should be easy to administer. Additionally, the host response to the immunogen should quickly reach maximal levels and result in a protective effect as quickly as possible following vaccine administration.

Traditional vaccines have typically used complex immunogens such as inactivated viruses or bacteria to evoke immunity. Such vaccines were often associated with adverse side effects (e.g. granuloma formation, pyrogenicity, and hypersensitivity). The use of subunit vaccines has reduced the number and severity of unwanted side effects associated with vaccines produced with more complex immunogens. Subunit vaccines are comprised of only one, or a few, proteins or polysaccharides from the target pathogen. Suzue et al in Experientia (77, 1996, pp451-465) teach heat shock proteins (HSPs) as subunit vaccines. Due to their small size, by themselves, subunit vaccines tend to be only weakly immunogenic, often failing to induce a satisfactory level of immunity. Thus to be effective, the use of subunit vaccines require strategies to enhance immunogenicity, such as the use of enhanced adjuvants and specific delivery strategies.

One strategy for improving the immunogenic response to subunit vaccines has been through the use of controlled release vaccine delivery by means of an implantable depot delivery system. Controlled-release technology provides improved efficacy by optimizing the temporal and spatial presentation of the antigens and adjuvants to the immune system. Controlled long-term release of the immunogen generally reduces the number of antigenic determinants needed to produce an effective vaccine and eliminates the need for booster shots. Ideally, controlled-release technology will mimic natural immune challenge by delivering an initial bolus of the immunogen, then gradually decreasing the amount of the immunogen released to the host. Controlled-delivery systems can efficiently direct antigens to antigen-presenting cells (APCs) to generate both cellular and humoral responses potentially leading to an optimal immune response in relation to the intended vaccine. Adjuvants, especially resorbable adjuvants, can serve as controlled-release devices to achieve complex pulsatile kinetics and antigen release. Zhao in the Journal of Pharmaceutical Sciences (85, 1996, p1261-1267) teaches controlled-release technology using polymers, with an emphasis on tumor vaccines.

In addition to controlled release strategies, vaccine immunogenicity has been augmented by specific adjuvant selection. Traditional vaccines as well as subunit vaccines have generally required the use of adjuvants. Typical adjuvants known to the art include aluminum compounds, muramyl dipeptide, and Freund's complete and incomplete adjuvants. Aluminum compounds and synthetic polymers have been used extensively as adjuvants, but they are non-resorbable and remain in the body after use, and the monomers used to produce synthetic polymers can be toxic (Pharmaceutica Acta Helvetica, 53, 1978, pp. 17-23).

Calcium phosphate materials are attractive as adjuvants and delivery vehicles because they are non-toxic, stable and biocompatible. Additionally, calcium phosphates are known to posses high affinity binding characteristics for antigens, vaccines, immunogens, proteins and other active agents. A method for preparing a calcium phosphate gel is described in Towey et al., U.S. Pat. No. 2,967,802. Towey suggests the use of these calcium phosphate gels as vaccine delivery vehicles or as immunological adjuvants, as well as tablet disintegrators; suspending agents; flocculating agents; oral detoxifying antacids and others; but fails to provide examples or otherwise enable these embodiments. However, there is no mention as to how to augment or heighten the immune response using the prepared gel. Additionally, Relyveld in U.S. Pat. No. 4,016,252 and [Developments in Biological Standardization, (65, 1985, pp 131-136) describes the production of an injectable calcium phosphate gel, which can adsorb vaccines. The purpose of Relyveld's calcium phosphate gel is to provide highly concentrated and stable vaccines, not to increase adjuvanticity.

Adjuvant particles may be used to effect adjuvanticity of a vaccine. Kreuter et al. reported in Vaccine (6, 1988. pp. 125-129) that a decrease in particle size diameter increased the adjuvant effect of a nanoparticle polymer. Grafe in Arzneim.-Forsch (21, 1971 pp. 903) and Kreuter in Infection and Immunology (19, 1978 pp. 667) reported similar findings using $Al_2O_3$ adjuvants and γ-ray-polymerized poly(methyl methacrylate) particle adjuvants, respectively. Courvreur et al in U.S. Pat. No. 4,329,332 describes synthetic polymeric nanoparticles which contain a biologically active substance that is released to a host at a rate similar to the rate of biodegradation of the polymers. Alemann et. al. in European Journal of Pharmaceutics and Biopharmaceutics, (39, 1993. 173-191) discuss that the continual problem with nanoparticles has been the rapid uptake by the reticuloendothelial system (RES). Since the RES functions to remove small foreign particles from the blood circulation, drugs contained on such particles do not reach their destination site, but rather are found in high concentrations in the liver and spleen. Kreuter in Journal of Controlled Release (16, 1991. pp. 169-176) teaches various methods to avoid RES nanoparticle uptake, such as the use of surfactants, magnetic fields and different administration routes (e.g. subcutaneous, intramuscular and ocular). After subcutaneous and intramuscular injection, nanoparticles treated in these ways stay at the injection site (Kreuter, Journal of Pharmaceutical Sciences, 72, 1983, p1146-1149). Also, drugs and antibiotics were shown to yield reduced toxicity and/or increased efficacy when combined with nanoparticles. It has also been reported by Gurny (Biopharmaceutics of Ocular Drug Delivery, CRC Press, Boca Raton, 1993, p81-90.) that the pre-corneal resident time of pilocarpine was increased after it was incorporated into nanoparticles. Amerongen et al in U.S. Pat. No. 5,443,832 also discloses that hydroxyapatite particles of suitable size (0.01 to 0.1 micron) can carry antigens across the epithelium but does not teach adjuvanticity of particle sizes. Further, hydroxyapatites have been known to be non-resorbable or poorly resorbable.

To date, a number of calcium phosphate adjuvants have been developed, but none have been optimized for adjuvanticity. A number of these calcium phosphate adjuvants suffer from one or more additional drawbacks, such as poor biocompatibility, low resorbability, inability to provide controlled release of an active agent, the need for multiple immunization and difficulty of administration. Furthermore, none have been amorphous calcium phosphates or nanocrystalline calcium phosphates. In fact, Olson reported in Biomaterials and the Immune System (Handbook of Biomaterials and Bioengineering Pt. A, Vol. 1, Marcel Dekker, New York, 1995), incorporated herein by reference, that ceramics and inorganic composites, including tricalcium phosphate, are believed to be immunologically benign. Thus, there is a need for an improved calcium phosphate delivery system that incorporates more desirable characteristics, together (e.g. resorbability, controlled release, biocompatibility, ease of administration). And, there is a need for improved biocompatible resorbable calcium phosphate adjuvants and delivery vehicles that will enhance or heighten the desired host response.

SUMMARY OF THE INVENTION

An amorphous calcium phosphate adjuvant is disclosed. A poorly crystalline apatitic calcium phosphate adjuvant is disclosed. A calcium phosphate adjuvant with an adjuvanticity enhancing means is disclosed. The enhancing means may be exogenous or endogenous and can be combined within a single adjuvant formulation.

DEFINITIONS

"Adjuvant"—"Adjuvant" refers to any substance that is capable of producing or enhancing a host response toward a specific active agent. At times, the adjuvant may elicit a host response alone, without the use of an active agent. "Adjuvanticity" describes any substance's ability to elicit a host response. Such adjuvants are described herein as having nonspecific adjuvanticity.

"Delivery vehicle"—"Delivery vehicle" refers to any substance that can carry or introduce an active agent to a host. A delivery vehicle may also be an adjuvant.

"Host Response"—"Host response" refers to the biological reaction generated by a host to a foreign or implanted substance, within a time period, after it is introduced to or recognized by the host. This reaction may be inflammatory, immunological, mitogenic, toxic, or any other reaction in response to the substance. The "host response" may be either adaptive or innate, though both are required for a fully functional response.

"Resorbable"—"Resorbable" is used to describe the elimination of a material from the host. The material can be "resorbed" by enzymatic processes, cellular reaction, dissolution or other biological or physical degradation mechanism. Resorption may take place over a time course from days to years. Resorption as used herein includes remodeling of a substance to bone.

"Antigen"—"Antigen" refers to any substance or active agent that when introduced to a host, elicits, by any means, a specific antibody response to the introduced substance.

"Active Agent"—"Active agent" refers to any substance that has biological activity. Active agents include such substances as antigens, vaccines, tolerogens, immunogens, growth factors, proteins, nucleic acids and others.

"Vaccine"—"Vaccine" refers to any substance that induces an adaptive host response, resulting in immunity or partial immunity to a pathogen. A vaccine may be without limitation a live, attenuated (non-pathogenic) or dead pathogen, an antigen or a subunit vaccine, which is only one or a few proteins or polysaccharides from a pathogen.

"Adjuvanticity Enhancing Means"—"Adjuvanticity Enhancing Means" is a substance, treatment or adjuvant configuration that results in an increased host response to an adjuvant as compared to the host response to the adjuvant in the absence of the adjuvanticity enhancing means. Increased adjuvanticity can often be measured as an enhanced or heightened aspect of some element of the immune or foreign body response (e.g. increase in a specific immune cell type such as, macrophages, CD4, CD8, lymphocytes or specific increases in humoral or cellular pathways).

The enhancing means may be exogenous or endogenous. "Exogenous enhancing means" are considered to be one or more additions to any prospective calcium phosphate delivery system which further increases the standard host response to that delivery system. An exogenous enhancing means can be applied to the adjuvant before, during or after manufacturing the calcium phosphate material of the adjuvant. Incorporation of such exogenous enhancing means can be accomplished in a similar fashion compared to the incorporation of active agents into the adjuvant (e.g. adsorption, mixing, covalent linkage). Preferred exogenous enhancing means include cytokines and adjuvants such as, muramyl dipeptide, aluminum hydroxide, aluminum phosphate, Freund's Complete Adjuvant, Freund's Incomplete Adjuvant, and polymers. "Endogenous enhancing means" refer to those alterations or enhancements of the adjuvant itself which lead to augmented adjuvanticity. Typically, the endogenous enhancing means are incorporated into the adjuvant during the manufacturing process, but such modifications can also be made after the adjuvant has been prepared. Examples of endogenous adjuvanticity enhancing means include but are not limited to increasing the degree of crystallinity within the calcium phosphate material, altering the specific chemical and/or phase composition according to the examples herein, increased roughness and the particle size and number (measured as volume percent) of the adjuvant material.

"Amorphous calcium phosphate"—"Amorphous calcium phosphate" (ACP) refers to a calcium phosphate material with significant amorphous character. Significant amorphous character contemplates greater than 75% amorphous content, preferably greater than 90% amorphous content, and is characterized by a broad, featureless X-ray diffraction (XRD) pattern.

"Poorly Crystalline Apatitic Calcium Phosphate"—"Poorly Crystalline Apatitic Calcium Phosphate" (PCA calcium phosphate) describes a synthetic poorly crystalline apatitic calcium phosphate. The PCA calcium phosphate material is not necessarily restricted to a single calcium phosphate phase, provided it has the characteristic XRD and Fourier Transfer Infra-red (FTIR) spectroscopy pattern. A PCA calcium phosphate has substantially the same XRD spectrum as bone. The spectrum is characterized by only two broad peaks at 2θ values in the region of 20°-35° with one centered at 26° and the other centered at 32°, and the absence of shoulders and sharp peaks at 2θ values of 27°-34°. In particular, there are no sharp peaks or shoulders corresponding to Miller's Indices of 210, 112 or 300. Shoulders may be presented at approximately 2θ values of 29° and 33.6°. It is further characterized by FTIR peaks at 563 $cm^{-1}$, 1034 $cm^{-1}$, 1638 $cm^{-1}$ and 3432 $cm^{-1}$ (±2 $cm^{-1}$). Sharp shoulders are observed at 603 $cm^{-1}$ and 875 $cm^{-1}$, with a doublet having maxima at 1442 $cm^{-1}$ and 1457 $cm^{-1}$.

"Nanoparticle"—The term "nanoparticle" used herein describes the physical diameter of an adjuvant particle. A nanoparticle ranges from 1.0 nm to 1000 nm or 1.0 μm. As discussed herein, adjuvant size refers to the average nanoparticle size, unless expressed otherwise, as determined by scanning electron microscopy.

DETAILED DESCRIPTION OF THE INVENTION

The present invention provides calcium-containing adjuvants and vaccine delivery vehicles which, when present alone or in combination with one or more active agents such as antigens or vaccines, elicit a host response or augment a host response towards the antigen or vaccine. The inventive adjuvants or delivery vehicles may provide continuous, delayed, sequential and/or intermittent depot delivery of an antigen or other active agent to a host. In other cases, the material may deliver a quick one-time dose of an active agent to a host.

Characteristics of the Calcium-Containing Adjuvant

The adjuvant is a calcium-containing material. Any calcium compound can be used, although calcium phosphates and calcium sulfates are preferred. Amorphous and poorly crystalline apatitic calcium phosphates are particularly preferred. In some instances, additional materials in conjunction with the calcium based adjuvants may be present to augment adjuvanticity. Generally, the calcium compound is formed into an injectable gel or solid nanoparticles. The preferred adjuvant or vehicle can be designed to absorb, bind, entrap or otherwise contain or present an antigen, subunit vaccine or other active agent. Useful calcium adjuvants include, but are not limited to, calcium sulfates and calcium phosphates such as amorphous calcium phosphates (ACP), poorly crystalline apatitic calcium phosphates (PCA), dicalcium phosphate dihydrate (DCPD), tricalcium phosphates (TCP), tetracalcium phosphate (TTCP), monetite, monocalcium phosphate monohydrate (MCPM), octacalcium phosphates (OCP), hydroxyapatites (HA). Carbonated or otherwise substituted versions of these calcium phosphates are also contemplated in the invention. A detailed description of the preparation and characteristics of suitable calcium phosphates useful as adjuvants in the instant invention can be found in co-pending application U.S. Ser. No. 08/729,344 entitled "Methods and Products Related to the Physical Conversion of Reactive Amorphous Calcium Phosphates" and U.S. Patents: Lee et al. in U.S. Pat. No. 5,683,461; and Lee et al. U.S. Pat. No. 5,783,217 which are all hereby incorporated by reference. LeGeros R. Z., in *Calcium Phosphates in Oral Biology and Medicine*, Karger Pub. Co., New York, 1991 lists additional useful calcium compounds.

Resorbability

In most cases, the inventive adjuvants are resorbable. Resorbability generally eliminates the need for surgical removal of the delivery vehicle, after completion of the vaccination process. Resorbable calcium adjuvants also allow the controlled delivery of active agents, such as an antigen, to a host at a specific rate. The antigen is generally delivered to a host at a comparable rate to the resorption rate. Custom designed resorbability characteristics of the inventive adjuvant provides for selected delivery rates for specific immunogens as required for the development of immunity. In preferred embodiments, weakly resorbing calcium adjuvants will be used to provide a slow release depot delivery of the antigen to the host. In other embodiments, the calcium adjuvant will be strongly resorbable and provide a means to deliver a fast, quick dose of the antigen to the host. In yet other embodiments, a combination of weakly and strongly resorbable calcium phosphates will be used to produce a variable or pulsatile kinetic release to mimic primary immunization and subsequent boosters. Example 34 demonstrates the use of a pulsatile delivery adjuvant in which the variable delivery rate is the result of a combination of adjuvants with differing resorption rates. The resorption rate, and therefore the delivery rate, can be adjusted to hours, days, weeks, months, and even years by varying the preparations of the variously resorbing components. In preferred embodiments, the adjuvant will be resorbed at the desired rate of antigen delivery.

The resorbability of the inventive adjuvant may be tailored according to the needs of a specific application. In some instances, the calcium-based adjuvant will be non-resorbable and will remain in the body indefinitely. Ceramic adjuvants, such as sintered calcium phosphate (e.g. highly crystalline hydroxyapatite), remain in the body after completion of vaccine delivery. In preferred embodiments, the adjuvant is resorbable. Resorbable adjuvants biodegrade over time, ultimately leaving little or no residual material in the body. Adjuvants may be either strongly resorbable or weakly resorbable. In preferred embodiments of the invention, a strongly resorbing adjuvant is characterized as follows: at least one gram (preferably 1-5 g) is implanted in a subcutaneous or intramuscular site, at least 80% of the adjuvant is resorbed within one year. In more preferred embodiments, one gram of adjuvant will be resorbed within nine months, six months, three months, and ideally one month or less. Weakly resorbable means that less than 80% of one gram of starting adjuvant is resorbed after one year. Resorption, as used herein, encompasses solubility based dissolution processes, as well as active cellular or enzyme based processes. Preferred calcium-based adjuvants are resorbed through active cellular or enzymatic processes. By controlling the rate of active degradation of the adjuvant, the inventive adjuvants can be tailored to have linear resorption rates.

Resorbability of the inventive calcium phosphate vehicles can be varied through the adjustment of one or more physical parameters including vehicle size, vehicle particle size, porosity, density, and/or crystallinity. Two or more of these parameters will generally be adjusted in concert to fine-tune the final resorption rate. Additionally, certain molecular factors may be incorporated into the vehicle that can be used to affect its resorption rate by influencing the cellular or enzymatic processes that ordinarily mediate vehicle resorption in the body. These incorporated factors are often biologically active molecules or collections thereof, which affect bone metabolic processes, such as the activity of osteoclasts and/or osteoblasts. In other instances the incorporated factors attract or otherwise affect the activity of one or more of macrophages, monocytes, or foreign body giant cells. Such useful factors include: growth factors, enzyme inhibitors, extracellular matrix components, cytokines and the like.

Ultimately, resorption rates will be established empirically by using intramuscular or subcutaneous implantation of the adjuvant in one or more small animal models to assess the exact effect of formulation adjustments on adjuvant resorption rates. In these model systems, a variety of candidate formulations may be tested simultaneously and resorption rates can be compared at various time points using standard histological, radiographic or other methods know to the art.

Adjuvant Preparation

Particle Size

In general, for a given calcium phosphate, smaller particles sizes will resorb more rapidly than larger particles. Monolithic devices, on the order of one gram will resorb more slowly than one gram of the same material when in particulate form. For precipitated calcium phosphates, particle sizes may be controlled by careful control of the precipitation speed. Rapid precipitation, followed by rapid harvesting of the precipitate, is useful in the production of small particle sizes (e.g.

particle size ranging from 5 nm to 150 nm). For example, the ACP as described in Example 1 (aged for 30 seconds) had a particle size range of 5 nm to 50 nm, as determined by scanning electron microscopy. Slower precipitation speeds, as well as the maintenance of the precipitate in the presence of the precipitants or mother liquid for longer periods of time, promotes the growth of larger particle sizes (e.g. particle size greater than 300 nm). For example, the apatitic calcium phosphate adjuvant described in example 13 (aged for 48 hours) had an average particle size of approximately 300 nm. The use of standard milling processes known to the art (e.g. ball mills, roller mills, jet mills) followed by precise sieving, will also be useful in preparing vehicles of specific size particles. In other instances materials prepared from emulsions or slurries, as described in the art, will produce useful particle size materials. Particle sizes of less than 1 μm, preferably less than 0.5 μm, are generally preferred for adjuvants and delivery vehicles intended to be resorbed within six months. In one preferred embodiment, ACP calcium phosphate particles are sieved to a average size of approximately 100 nm and are capable of resorbing in less than three months.

In the most preferred embodiments of the invention, where maximum adjuvanticity is desired, it will be preferable to use minimal particle sizes on the order of angstroms or nanometers. In these instances, the use of further particle size adjustment to regulate resorption rate may not be feasible and it may be more advantageous to further control, or fine-tune, resorption rates by altering other physical parameters, such as adjuvant density or crystallinity or through the addition of proteins or growth factors which affect resorption rates.

Density

Vehicle density also has a significant effect on resorption rates. Density is most easily controlled by compression of the adjuvant following fabrication. Compressive forces of 8 MPa to 50 MPa may be applied through the use of molds and presses. In addition to compression, a variety of other methods, which are useful to adjust vehicle density, are known to the art and may be used. Calcium phosphate density for the inventive adjuvants and vehicles is best determined using pycnometry, such as Helium pycnometry (HP density). Calcium phosphates prepared with HP densities of approximately 3.0 gm/cm$^3$ will be useful for the production of slow resorbing vehicles. More rapid resorbing vehicles may be prepared from calcium phosphates with HP densities generally in the range of 2.5-2.8 gm/cm$^3$, preferably 2.5 gm/cm$^3$. HP densities with values less than 2.5 gm/cm$^3$ are often preferred for vehicles that are intended to resorb particularly rapidly.

Crystallinity

Generally, careful control of the adjuvant's degree of crystallinity and crystal size may be used to affect the overall vehicle resorption rate. For apatitic calcium phosphates with calcium to phosphorous ratios of 1.3-1.75, poorly crystalline forms are believed to resorb more quickly than highly crystalline forms. Highly crystalline stoichiometric hydroxyapatite (e.g., NIST® catalog #2910) is an example of a weakly resorbable vehicle. For other calcium phosphates, for a given calcium to phosphorous ratio, more amorphous forms will generally be more soluble than more crystalline forms. Increased resorption rates may be achieved through the production of apatitic calcium phosphates containing lattice defects, such as ionic vacancies or substitutions. Preferred embodiments include carbonated or otherwise calcium deficient apatites, all of which tend to have increased in vivo resorption rates. Further guidance for the production of similar such apatic calcium phosphates can be found in *Structure and Chemistry of the Apatites and Other Calcium Orthophosphates*, (Elsevier, Amsterdam, 1994, by J. C. Elliott), and the references contained therein, all incorporated herein by reference.

Porosity

The inventive delivery vehicle can be of any porosity that provides the desirable characteristics for immunogen delivery. Porosity facilitates both the diffusion of substances to and from the inventive material and, in certain applications, the penetration of cells and cell processes into the material matrix. Accordingly, adjuvants of lower porosity tend to resorb more slowly in vivo than those of higher porosity; therefore, the greater the porosity, the greater the rate of resorption. In one embodiment of the invention, porosity is increased through the use of a dry mixture of controlled particle size reactants. For example, the material described in examples 1-16, a reactant with a larger particle size (e.g. 300-500 μm) will produce a more porous material. In other embodiments, chemical or physical etching and leaching techniques are employed to vary the porosity. In one preferred embodiment, NaCl crystals (e.g. 50 μm-500 μm) are incorporated, into the paste material, by manual pressing and prepared according to Example 16. The size of the crystals used, is selected according to the desired pore size. Generally, the amount of crystals will be less than 20% by weight. The paste material is allowed to harden and the NaCl crystals are washed from the hardened material using a suitable aqueous liquid to solubilize the crystals such as distilled water or saline. Surface pores or macrovoids the size of the original NaCl crystals will result from such a treatment.

In addition to the percent porosity of a given vehicle, the pore size distribution is also important with regard to resorptive properties. The presence, or absence, of large particle pores (macrovoids) (e.g. 50 μm or greater) may have significant effects on resorption rates. Such macrovoids can facilitate cellular resorption. In preferred embodiments of rapidly resorbing vehicles, macrovoids of 50 to 300 μm diameter will be present. In some embodiments, the percentage of macrovoids in the vehicle, will be twenty percent (20%) or greater of the total volume. In many embodiments, less than ten percent (10%) of the vehicle volume will be composed of macrovoids. In some slower resorbing embodiments less than one percent (1%) of the vehicle volume will be represented by greater than 50 μm diameter macrovoids. Macrovoids can be incorporated through the use of leachable solid porogens during adjuvant preparation such as crystalline, particulate and/or fibrous sugars, starches and/or salts. In one preferred embodiment, NaCl crystals 200 μm-300 μm in diameter to the calcium phosphate of examples 16 and 17 at proportions of 20% weight percent. These porogens may be leached from the adjuvant, post fabrication.

Incorporation of Resorption Factors

Incorporation of factors, which attract or inhibit osteogenic cells and/or macrophages, can have a significant effect on adjuvant resorption rate. Thus, incorporation of bone morphogenetic protein into the inventive adjuvants will lead to more rapid resorption of the vehicle, particularly in soft tissue implant sites. Additionally, factors that attract osteoclasts (e.g. interleukin-1, lymphotoxin, calcitonin,) may be used to promote degradation of the vehicle. Osteoclast or macrophage activity inhibitors (e.g. neutral phosphate, glucocorticoids, plicamycin, gallium nitrate) may be used to prolong the resorption process. Extracellular matrix components, such as laminen, RDG peptides, collagen, fibronectin may also be included with the adjuvants. Further guidance regarding specific factors useful in the regulation of calcium phosphate resorption rates can be found in PCT/US97/18528, incorporated by reference herein. Generally, these factors will be incorporated into the inventive adjuvants as a concentration of less than 20% wt/wt preferably less than 10% and in most embodiments, less than 5%.

In many instances, adjuvant resorbability is preferred; however, it is not always required or desired. In some embodiments the inventive adjuvanticity enhancement can be obtained with a calcium adjuvant that is either weakly resorbable or non-resorbable. A non-resorbable adjuvant may be used when prolonged antigen delivery will occur over a matter of several years. A non-resorbable adjuvant may also be desirable in cases when the adjuvant is used additionally as a support matrix for tissue repair or growth, as a treatment for a disease, or for vaccination purposes. Non-resorbable calcium phosphate adjuvants can remain in the body without detrimental effects to the host due to their excellent biocompatibility. Alternatively, non-resorbable adjuvants may be surgically removed following the desired delivery period. Suitable non-resorbable or weakly resorbable calcium phosphate adjuvants include those prepared from sintered hydroxyapatite.

Adjuvanticity

Adjuvanticity denotes the level of effect an adjuvant has in eliciting an immune response. Any modification to the adjuvant or delivery vehicle that induces an altered immune response by the vehicle is considered to have effected its adjuvanticity. Adjuvanticity enhancing means can be used to induce specifically increase one or more of the cellular immune response, the humoral immune response or any other response to the antigen or other foreign substance. Suitable modifications to the delivery system that are capable of affecting adjuvanticity may include: alterations which affect cellular recognition of the adjuvant, cellular recognition of the immunogen and, in some cases, adjuvant biocompatibility. Exogenous alterations include the incorporation into the adjuvant of immuno regulating molecules (e.g. fas-L) which locally alter the immune response. Other parameters endogenous to the adjuvant may be altered to effect cellular recognition including: particle size, particle shape, particle roughness, specific surface area, pH, porosity, chemical reactivity/pyrogenicity. However, preferred embodiments often involve a combination of the aforementioned parameters, which arranged in such a fashion as to create a desired host response.

Particle Size

Adjuvant particle size can be adjusted to endogenously vary the adjuvanticity of the calcium-based material. The calcium phosphate delivery vehicle may comprise or be delivered in the presence of nanoparticles prepared from the same or similar materials as the adjuvant itself. Most often these particles will also contain the immunogen. The presence of nanoparticles has the effect of augmenting the host response to the immunogen. In preferred embodiments, nanoparticles comprise 1-100% of the adjuvant. In more preferred embodiments, nanoparticles comprise 25-100% of the adjuvant. Optimally, nanoparticles comprise 50% to 100% of the adjuvant.

A calcium salt of any particle size that directly elicits an enhanced response from a particular immune system can be used as the adjuvant. Example 28 demonstrates the use of varying particle size to augment a specifically desired host response. Generally, to effect the adjuvant activity of the present invention, the preferred adjuvant particle size ranges from about 0.1 nm to about 50 µm. In more preferred embodiments, the particle size ranges from about 0.1 nm to about 900 nm, more preferably 1.0 nm to about 500 nm, and most preferred from about 100 nm to about 250 nm. Optimally, the particle size ranges from about 20 nm to about 80 nm. In some cases ranges of 5 to 50 microns have been useful to enhance adjuvant activity. Larger particles (50 µm or greater) typically employ other adjuvanticity enhancers, such as cytokines, other adjuvants or physical parameters (e.g. porosity), are included to enhance the host reaction.

Depot delivery systems with varying particle sizes may be used to avoid rapid RES uptake and thereby providing a more efficient delivery method. For those embodiments where a specific immunogen is adsorbed or covalently linked to the adjuvant, the release profile of the immunogen from the adjuvant exhibits sensitive dependency on particle size. Small particles (e.g. nanoparticles) can release the antigens at a higher rate than larger particles because of their larger surface-to-volume ratio. The larger particles (e.g. microparticles) can not be engulfed by phagocytic accessory cells until they are degraded into smaller particles; therefore, the larger particles serve as a depot of continuous antigenic stimuli. The rate of antigen release from these larger particles is at least indirectly dependent on the resorption rate of the particles themselves. In one embodiment, a combination of small and large particles may create a pulsatile pattern of antigenic release, thereby mimicking the antigen concentration profiles typically seen during immunization scenarios that utilize an initial primary shot and followed by a number of booster shots.

Particle Shape

The shape of the individual particles and of the adjuvant itself may endogenously affect the adjuvanticity. Generally, ACP adjuvants contain particles that appear spherical and/or sometimes fused. Spherical ACP particles are prepared according to Example 1. PCA calcium phosphate particles are usually needle-like in appearance. Adjuvants containing needle-like particles will generally produce a greater response when compared to adjuvants containing only platelet-like or spherical particles. In some preferred embodiments, the adjuvant will comprise needle-like particles prepared according to Example 12. In other cases, both spheres and needles, as well as plate-like particles may be used. Adjuvant particles prepared according to Example 13 represent the combination of different particle shapes.

Particle Roughness

Adjuvanticity may also be endogenously controlled by adjusting particle roughness, which is described as the physical surface morphology, or relief patterns, of the individual particles comprising the adjuvant or the adjuvant itself. Parameters involving such factors as porosity, crystallinity and etching may be employed to adjust particle roughness. The degree of surface roughness is known to have specific effects on biocompatibility, with extreme surface roughness being associated with decreased biocompatibility. Ideally, in preferred embodiments, an adjuvant will be biocompatible yet be capable of enhancing an immune response. In some cases, however; it may be acceptable by increasing surface roughness to sacrifice some level of biocompatibility to achieve a higher adjuvant activity. For example, Nagase in Host Reaction to Particulate Biomaterials (Handbook of Biomaterials and Bioengineering Pt. A, Vol. 1, Marcel Dekker, New York, 1995), incorporated by reference, describes a calcium phosphate material with higher crystallinity than bone that may induce a greater host defense reaction. Total surface area, as well as surface roughness, are enhanced by increasing porosity and/or pore size. Shanbhag recently reported (Journal of Biomedical Materials Research, Vol. 28, p81-90, 1994) increasing IL-1 levels corresponding with higher surface areas of titania and polystyrene particles. A larger surface area will promote an increased immune response. Particle surface area, reported as the surface area per gram (specific surface area), can be measured by gas sorption. The Chem- BET®3000, which is available from Quantachrome Corporation, measures surface area by flowing various mixtures of nitrogen and helium over the particles and cooled with liquid nitrogen.

Particle roughness is further characterized by the amplitude or depth of etches found on the surface of the adjuvant. Particle roughness may be influenced by the shape of the particles (e.g. spheres, needles, platelets) comprising the adjuvant. In some embodiments, the degree of particle roughness may affect the recruitment of desired cells or immune response (e.g. cellular and/or humoral activity). An adjuvant comprising particles with a greater degree of roughness is generally more likely to attract desired cells than an adjuvant with smooth particles. The immune system responds to any foreign body introduced to a host. An adjuvant (foreign body) with a roughened surface (peaks and valleys) will seem more threatening to the host, causing a greater immune response for complete protection or attack. Additionally, in other technologies, such as bone growth, surface roughness provides an improved adhesive structure, or scaffold, for the attachment of bone forming cells (Suzuki, 1997). This concept is adapted to the surface of an adjuvant to attract and secure cells associated with the immune response. The degree of particle roughness can be determined by scanning electron microscopy as well as other sophisticated surface measurement instrumentation. In preferred embodiments, a loaded adjuvant with a rough surface will provide an adhesive structure for the attachment of desired immune cells (e.g. antibodies).

pH

In most cases, the adjuvant's pH is neutral and will not by itself elicit a host response. Adjuvant pH will be varied depending on the application of the adjuvant and the antigen in use (the stability of certain antigens is affected by pH). Generally, adjuvant pH is about 4.0 to about 10.0; more preferably, pH values should be about 6.0 to about 9.0. In some embodiments, adjuvant pH may be more acidic (e.g. 0-3) or basic pH (e.g. 11-14), in order to elicit a pyrogenic or cytotoxic host responses.

In preferred embodiments, the endogenous pH of the calcium-based adjuvant is adjusted with raw materials or precursors during manufacturing. The preparation and ratios of starting materials can be varied to control the pH of the adjuvant. In other cases, the pH of the precipitate or gel can be adjusted. In preferred embodiments, calcium salts will be selected with $pK_a$s at or near the desired pH of the adjuvant. In other embodiments, the pH is lowered by adding an acid or acidic buffer (e.g. phosphoric acid, hydrochloric acid, monobasic sodium phosphate acetic acid) or the pH is raised by adding a base or alkaline buffer (e.g. potassium hydroxide, calcium hydroxide, sodium hydroxide), or through the use of buffering agents with $pK_a$s in desirable ranges as is known in the art. In yet other embodiments, the pH of an adjuvant in paste or slurry form can be controlled by introducing specific pH buffered solutions as hydrating agents. Since extremes of pH may weaken the electrostatic interactions of the antigen-to-antibody binding, in preferred embodiments, the pH of the adjuvant will correlate with the pH of the antigen-to-antibody complex. However, in rare embodiments, the adjuvant biocompatibility may be sacrificed and the pH extended to extreme values, in order to aid adjuvant activity.

Selective Immune Response Enhancement

A variety of enhancement means, both endogenous and exogenous may be used to augment, enhance or, in some instances, suppress specific components of the immune response. Macrophages (e.g. Mac-3), T cells (e.g. CD3ε, CD4, CD8α) and B cells (e.g. CD45R/B220) may be selectively augmented after injection or implantation of different calcium phosphate adjuvants (Example 18), which by virtue of their specific formulation, have endogenously enhanced adjuvanticity. Manipulation of specific immune response components can also be affected through a choice of: administration routes, adjuvant combinations, antigen usage, immunizing in the presence of cytokines, and/or using various carriers. To apply these approaches of adjuvant manipulation for a particular vaccine, it is helpful to identify which component of the immune system to target (e.g. humoral or cellular). Eventually, all components of the immune system function to protect the body from an attack, but in some cases, it is desirable to first elicit one component over the other. For example, eosinophils are desired to protect against parasitic infections and mast cells are important in allergic responses. Additionally, the T-helper cell types may be elicited when a cell-mediated immune response is desired and B-cells may be elicited when a humoral response is desired. Additionally, CD8 cells may be recruited or cytokines may be incorporated with the adjuvant when targeting tumor tissue since these cell types are known to combat tumor tissue. Once the desired type of cell response is identified, the above parameters may be adjusted as described herein, to elicit an enhanced response from the desired cell or cell types. Table 1 in Example 18 provides guidance for selecting an appropriate adjuvant formulation, based on the desired immune response. The level of cellular immune response is indicative of the adjuvant activity of the prepared calcium phosphate adjuvant, the higher the response, the greater the adjuvant activity. For example, a specific ACP adjuvant (prepared according to example 7) is used to elicit an augmented B-cell and macrophage response. Further guidance can be found in Golding (Annals New York Academy of Sciences, 754, 1995, p127-137) and Newman (The Journal of Immunology, 148, 1992, p2357-2362).

Example 24 describes the use of exogenously added cytokines/adjuvant combinations used to combat tumors. A persistently high concentration of cytokines (e.g. IL-2, IL-4, IL-6, IFN-γ, TNF-α, GM-CSF) in the vicinity of tumor cells is known to stimulate antitumor activity by amplifying the immune response to the tumor by both antigen-specific and nonspecific T cells. By coordinating the immune response with the appropriate inventive adjuvant, cytokine gene-based cancer vaccines induce long-term systemic antitumor activity, in addition to generally eradicate injected tumor cells. The exogenous incorporation of cytokines, such as gamma interferon and IL-12, into the inventive calcium phosphate adjuvants may boost both the humoral and cellular responses to an incorporated antigen. IL-1 increases antibody production by directly stimulating B lymphocytes and is known to potentiate T-cell proliferation by increasing the production of IL-2. IL-6 has the ability to stimulate immunoglobulin production. IFN-γ activates helper T cells. IL-12 has been demonstrated to increase cell-mediated immunity for the control of virus infections. Further guidance for the use of cytokines in adjuvants can be found in Vaccine Design, (Powell, Plenum Press, New York, 1995) and ImmunoBiology, Appendix II, (Current Biology Ltd./Garland Publishing, New York, 1996) incorporated in their entirety by reference. Controlled-release calcium phosphate adjuvants are particularly useful for the delivery of cytokines to regulate or inhibit tumor growth. Antigen encapsulated in large microspheres (20-40 μm) can be used for slow release of the antigen, while antigens encapsulated in submicron particles (<1 μm) can be used to induce rapid macrophage uptake and processing. The use of an adjuvant which specifically induces cytokine release, thereby results in a response augmentation is also considered to be within the scope of this invention.

In some embodiments, the calcium-based adjuvant may be prepared in combination with an exogenous adjuvanticity enhancing means. More specifically, an adjuvanticity enhancer may be another known adjuvant, such as aluminum hydroxide, aluminum phosphate, muramyl dipeptide, biodegradable polymeric microspheres, liposomes and others. For example, Complete Freund's adjuvant (CFA) activates Th1 cells resulting in delayed-typed hypersensitivity, while alum activates Th2 cells, initiating a humoral response. Since each adjuvant alone provides a unique response, a combination of adjuvants may provide for an even more potent immune response than from a single adjuvant. Such an adjuvant combination would be made of separate components, that are added to augment a particular type of immune response, resulting in an additive or synergistic final effect. For example, the calcium-phosphate adjuvant of the present invention with the appropriate characteristics to elicit a humoral (B-cell) response (prepared according to Examples 1,3 and 5 may be combined with muramyl dipeptide, which is known to induce a cellular (T-cell) effect, thereby producing a complete host response. Many determining factors, such as the choice of antigen and desired adjuvanticity will determine the appropriate combination of adjuvants. The inventive calcium phosphate adjuvant will serve as the base or primary adjuvant and the source of any endogenous response enhancement; additional exogenous adjuvanticity enhancers will be added for their specific biological responses. In preferred embodiments, the calcium phosphate material (prepared according to Examples 1-17) will comprise >50% of the adjuvant, more preferably, >75% and most preferably, >90%. The remaining adjuvant components can be chosen singularly or in combination. In this manner, the adjuvant will be fashioned according to the specific vaccination requirements and the desired response. In most cases, embodiments employing aluminum hydroxide will involve non-resorbable or poorly resorbable calcium phosphate adjuvants. Muramyl dipeptide may be incorporated into the calcium phosphate adjuvant to enhance or augment the host response, more specifically, cellular immunity. Additionally, other adjuvanticity enhancers such as QS-21 and MPL-A can be added to induce cellular response.

Liposomes and polymers (e.g. PMMA, PLGA, PLA, gelatin, poly(phosphazene)), particularly biodegradable polymers, may also increase adjuvant activity by themselves serving as a delivery vehicle for the inventive calcium phosphate adjuvant. Additionally, liposomes and polymers are considered to have adjuvant potential as reported by Glück in Liposomal Presentation of Antigens (Vaccine Design, ed. Powell, Plenum Press, New York, 1995). In a preferred embodiment, a liposome or polymer will encapsulate the calcium phosphate adjuvant, producing microspheres. Methods of encapsulation, using polymers and liposomes, are well known to those skilled in the art. The size of the microspheres is controlled during manufacturing. The coordinated use of smaller microspheres (<10 μm) and larger microspheres (>10 μm) will create the pulsatile kinetics of antigen release typically seen with primary and secondary immunizations and boosters, respectively. The antigen may be combined (incorporated or adsorbed) with the liposome or polymer, the calcium phosphate adjuvant or both. The calcium phosphate/liposome adjuvant may also entrap any substance that will improve the vaccine, such as desired cytokines, other adjuvants, and composite materials.

Composites

In some instances, it may be desirable to alter specific physical properties of the calcium-based adjuvant to an extent not possible with the pure adjuvant material alone. In such instances, the adjuvant may be used in a composite form through the addition of one or more supplemental materials. A supplementary material is a substance that is added to the inventive adjuvant and alters a physical property or characteristic of the adjuvant such as tensile strength, elasticity or flexion. In some instances the supplemental material may also serve as an enhancing means. The supplemental material may be supplied in any suitable form (e.g. particulate, fiber). In preferred embodiments, the supplementary material is added to the inventive calcium phosphate adjuvant at volume fractions of 1-50% and more preferably, 1-20% either during synthesis or after manufacturing. In embodiments that encompass resorbable calcium phosphate adjuvants, it is preferred that the supplemental material is bioresorbable as well; however, the resorption rates may vary.

Composite adjuvant systems may be designed with delivery kinetics similar to those observed with traditional primary/booster immunization strategies. In such embodiments, the antigen is released at calculated intervals and/or rates, to induce proper antibody response levels associated with optimal immunization. Such composite adjuvants are useful since they comprise the desirable characteristics of both more resorbable and less resorbable adjuvant. As an added option, the relative ratios may be varied to produce vehicles of differing resorption profiles. In some embodiments, composites will improve one or more additional properties of the adjuvant related to its manufacturing, surgical, or in-storage characteristics.

The preparation of the inventive calcium phosphate adjuvants as composites requires the addition of one or more supplemental materials to the adjuvant. The supplementary materials may themselves be a composite. The supplemental materials may serve as a matrix for the calcium adjuvant, which is embedded or dispersed within the matrix. Alternatively, the calcium adjuvant may serve as a matrix for the supplemental materials, which are then dispersed therein. In a preferred embodiment, the calcium-based adjuvant is combined with poly-L-lactic acid (PLLA) and/or polyglycolide (PGA) for increased flexibility. Guidance for the production of calcium phosphate composites may be found in co-pending application Ser. No. 08/732,016, herein incorporated by reference. In a preferred embodiment, a calcium phosphate adjuvant is prepared as a composite of calcium phosphates with different resorption rates (see example 34). Variable delivery kinetics may be achieved by combining multiple calcium phosphates having different resorption rates within one adjuvant system.

Strength and Elasticity

Adjuvants with desired mechanical properties (e.g. strength and elasticity) may be prepared as calcium phosphate composites. For specific implantation sites, it may be desirable to have a flexible adjuvant that will bend or twist (e.g. subcutaneous location or intrathecal locations). In other instances, a more rigid adjuvant is desirable (e.g. in the abdominal cavity or central nervous system). In general, methods known to producers and manufacturers of composite materials will be useful in these cases. Supplementary materials, such as fillers and binders known in the art, can be used to alter the strength and elasticity of the composite calcium adjuvant. In one preferred embodiment, 10-20% by volume of Dextran® (supplied by Sigma® Chemical Co.) is added to the inventive calcium phosphate adjuvant to add flexibility. Increased amounts of Dextran® will increase the degree of flexibility.

The instant invention offers a method to fabricate the adjuvant particles in a way such that the RES will not intercept the delivery of the active agent. Specifically, the recruitment of specific appropriate immune cells may be augmented because RES uptake of the inventive adjuvant is avoided through the use of surface treatments, coatings, surfactants and/or magnetic fields. Non-ionic surfactants such as poloxamers (e.g. Poloxamer 188 and Poloxamer 338) have been used to coat the surfaces of nanoparticles to delay RES uptake. In a preferred embodiment, the calcium phosphate adjuvant/immunogen-nanoparticles are suspended in saline or water containing 1 % of the chosen poloxamer, which adsorbs strongly to the surface of the nanoparticles. The coated particles are particularly useful for intravenous administration. Coated particles are more likely to reach other target sites (e.g., tumor tissue) than uncoated particles, especially when injected intravenously. Other suitable coatings and surfactants known in the art may also be useful for directing antigen-loaded particles to desired sites. Further guidance for using surfactants can be found in Illum (FEBS Letters, 167, 1984. p79-82) and Leu (Journal of Pharmaceutical Science, 73, 1984. p1433-1437).

In some cases, it may be desirable to combine magnetic materials with the inventive calcium phosphate adjuvants to guide the controlled delivery of the active agent to the target site. A magnetic field is placed around the target to improve efficacy. The magnetic adjuvant particles are attracted to the magnetic field and tend to concentrate around the target, thereby delivering the active agent focally to the appropriate site. In one example of this embodiment, the calcium phosphate adjuvant/antigen-nanoparticles are combined in distilled water or saline with an appropriate amount of magnetite. The coated nanoparticles are administered intravenously. In most cases, tumor sites are specifically targeted although any site can be chosen. Further guidance for using magnetic materials can be found in Widder (European Journal of Cancer and Clinical Oncology, 19, 1983, p135-139 and p141-147) incorporated herein by reference.

In other embodiments, composites of calcium salts and any additional materials are prepared as a paste by the addition of a fluid to a mixture of the calcium adjuvant and the supplemental materials. The paste is then hardened by drying or in conjunction with a hardening reaction.

Manufacturing the Adjuvant

The calcium adjuvants of the present invention can be manufactured to resorb and/or deliver immunogens according to the desired need. Parameters that may be adjusted according to need include: surface treatments, porosity, particle size, and others. Calcium phosphates, such as hydroxyapatites, prepared under low temperature conditions and PCA calcium phosphates are preferred adjuvants, along with amorphous calcium phosphates. The preparation of these calcium phosphates is described respectively in co-pending U.S. Ser. No. 08/554,817 and issued U.S. Pat. Nos. 5,650,176 by Lee et al., 5,676,976 by Lee et al., and 5,683,461 by Lee et al., and examples 1-17 herein. In preferred embodiments, the adjuvants are prepared as a gel, paste, pellets, gauge/mesh or sintered blocks. Gels are generally formed by precipitation. The precipitate aging time is varied to produce different particle sizes. Generally, the longer the aging time the larger the particle size. In some embodiments, after filtration and washing, the gel can be used as the adjuvant material. In other embodiments, the gel is mixed with an aqueous medium, such as physiological/sterile saline or water, at various concentrations to make a paste or putty. In yet other embodiments, the gel is lyophilized to form a powder. The powder is mixed with an aqueous medium, such as saline, at different concentrations to form a paste or putty. The paste or gel can be allowed to harden. In preferred embodiments, an apatitic calcium phosphate adjuvant will harden at about 37° C., or body temperature. The hardened material can be broken, ground, milled or crushed to form particles of various sizes. The particles sizes can then be modified or adjusted as discussed above. These calcium compounds can be configured as adjuvants by combining active agents by any suitable means known in the art (e.g. through adsorption, co-precipitation or through the use of binders or fillers).

Adjuvants can be prepared with specific particle size or particle size distributions. When preparing an adjuvant gel from the precipitation reaction the crystalline structure and accompanying particle size can be controlled during maturation and/or with temperature. For the purpose of this disclosure, maturation is considered to be the aging time of the precipitate, while in contact with the mother liquid. In preferred embodiments, the particle size is increased by increasing the maturation times of the gel. More crystalline apatitic calcium phosphates require a longer maturation times, compared to more amorphous forms which require shorter maturation times. Higher temperatures usually yield more crystalline particles.

Alternatively, the gel can be lyophilized to form a dry powder. The powder's (either lyophilized or non-lyophilized) particle size can be controlled by sieving, milling and treating with different temperatures. Sieving the powder allows the particles to be separated according to size, usually from smallest to largest. In preferred embodiments, the powder is milled. In most cases, a longer milling time results in a smaller particle size. In other embodiments, the powder is heated to different temperatures. Higher temperatures (e.g. 400° C.-600° C.) can be employed to increase the crystallinity of ACP powders. However, for temperatures up to about 450° C., the amorphous character of an ACP is preserved, but the specific surface area decreases, which marks a decrease in particle size. In other embodiments, a hardened form of the calcium-based adjuvant may be broken down into particles by milling, pulverizing and other methods. Fine powders of the nanometer or less size range (e.g. ACP), can be compressed in a mold (e.g. compressive strength: 500 psi), then milled and sieved to achieve desired particle sizes. Other methods known in the art used to control particle size are considered to be within the scope of the invention.

Loading the Calcium Phosphate Adjuvant with the Active Agent

The adjuvant can be combined with one or more active agents, immunogens as well as adjuvanticity enhancers. The active agent with additional moieties may be combined with the calcium-based adjuvant through dissolution, adsorption, co-precipitation, centrifugation in a hydration medium, encapsulation, diffusion based processes, or any method known in the art. In preferred embodiments, the active agent is adsorbed during manufacturing onto calcium adjuvants in the presence of a buffering system compatible with the specific active agent. In preferred embodiments adsorption will occur under condition of relatively low ionic strength (e.g. 0.001 M-0.2 M NaCl) in the presence of minimal buffer concentration (e.g. 0.001 M TRIS pH 7.0) and generally with the presence of little or no phosphate ions (e.g. <0.1M). Further guidance, incorporated herein by reference, for adsorbing active agents can be found in Relyveld in U.S. Pat. Nos. 3,925,545 and 4,016,252 and Relyveld in Developments in Biological Standardization (65, 1985, pp. 131-136). Towey et al., in U.S. Pat. No. 2,967,802, describes the method of preparing a calcium phosphate-antigen gel composition. In a preferred embodiment, particularly useful for proteins and nucleic acids that adsorb well to calcium phosphates, a calcium phosphate adjuvant (prepared according to Example 16) will be placed in a buffered low ionic strength (e.g. 0.001M NaCl; 0.01 M TRIS pH 7.4) aqueous medium that contains the nucleotide or protein immunogen. The concentration of the nucleotide or protein immunogen will vary, usually less than 10.0 mg/ml. The immunogen will be adsorbed onto the surface of the adjuvant. The adjuvant may then be rinsed to remove any immunogen that was not fully adsorbed onto the surface.

In embodiments in which the adjuvant is prepared as a precipitate, paste or gel that subsequently solidifies and/or hardens, the active agent may be prepared integrally with the vehicle. Specifically, the agent may be suspended in a solution, usually a buffered solution in which biological activity of the agent is retained or augmented, and in which the hardening process may occur. This solution is then mixed with the adjuvant's precursors to form a paste, gel or solid, or it is added to the precipitate reaction and co-precipitated with or otherwise entrapped by or in the resulting precipitate. The active agent then becomes an integrated element of the adjuvant. Following completion of adjuvant fabrication, the adjuvant/vehicle is then implanted into the recipient. Such finished adjuvant/vehicles are generally in the form of a single device or it is in particulate form.

In other embodiments, the active agent is entrapped in the inventive calcium-based adjuvant. The active agent may agglomerate with the adjuvant particles, to form a particle/agent agglomerate. In yet other preferred embodiments, the active agent is otherwise attached to the calcium adjuvant. The attaching methods include, but are not limited to, dipping, rolling, spraying, pressing, gluing, pasting, and painting. Alternatively, the active agent and/or other moieties may be present in fillers or binders used in device fabrication. These methods and others are well known in the art. Chemical bonding (covalent, ionic, and hydrogen) is another method used to combine the adjuvant and the antigen. In one preferred embodiment, the immunogen is covalently attached, by methods known in the art, to the vehicle through the use of a linker which is sensitive to proteolysis.

In yet another embodiment, the antigen and other moieties if present, will be encased or encapsulated by the adjuvant. In such embodiments, the adjuvant will act as a capsule for containing the antigen. Since the adjuvant is resorbable, the antigen will be introduced to the body when the adjuvant is depleted, providing the host with a dose of antigen. In some embodiments, the finished adjuvant vehicle/device will contain the active agent in a layered form. Such layers can be designed so the active agent is released sequentially from the layers allowing the administration of multiple doses. Generally, devices prepared in this format will rely on solubility characteristics of the layers for proper delivery characteristics. In still other embodiments where the adjuvant is both permeable and resorbable, the encapsulated immunogen will diffuse out of the adjuvant/vehicle in a controlled delivery fashion until the encapsulation is breached by resorptive processes. At such time any remaining immunogen is released in a final delivery pulse. Specific embodiments for the production of vehicles employing layered architecture or encasing active agents using solid free-form technology as described by Cima in U.S. Pat. Nos. 5,490,962 and 5,518,680, incorporated herein by reference. Solid free-form technology can modify the adjuvant properties (e.g. release rates, adjuvanticity properties) by changing the three dimensional shape of the adjuvant. This technology is useful for controlled release of a bioactive agent and implantation and growth of cells. In one solid free-form embodiment a resorbable calcium phosphate powder such as is described in issued U.S. Pat. No. 5,676,976 by Lee et. al., incorporated herein by reference, is used as a matrix to encapsulate less resorbable calcium phosphate powders; which have been preloaded with an immunogen. The immunogen is also present in the matrix. The presence of the slower resorbing calcium phosphates insures the long term delivery kinetics of the immunogen.

In some embodiments, it may be desirable to modify the surface of the calcium adjuvant in order to improve the interface between the adjuvant and the active agent. The adjuvant may be subjected to surface treatments, such as plasma etching or sputter coating to alter the interfaces between the two phases as is known in the art. Surface treatments may be used to increase or enhance the affinity of the adjuvant for active agents such as proteins. Plasma etching may provide an altered or rough adjuvant surface which may modify device biocompatibility or the binding characteristics of an active agent or other moiety to the adjuvant. Further guidance for methods and applications utilizing plasma etching can be found in pending application U.S. Ser. No. 09/008,650 incorporated herein by reference.

Particle roughness often plays an important role when combining the active agent, such as the antigen, to the adjuvant. In most cases, increased particle roughness will enhance the binding capacity of the active agent to the calcium phosphate adjuvant. In other cases particle roughness may be controlled to affect the ability of cells (e.g. macrophages) to interact with the inventive adjuvant. The inventive adjuvant can be designed to recruit appropriate immune response cells and an appropriately rough surface will enhance the attachment of those cells to the adjuvant-antigen structure. Particle roughness can vary according to aging time of the precipitate material or crystallinity, in addition to surface treatments such as etching, coating and solid free-form technology, as described within.

The degree of crystallinity of the inventive adjuvant will impact attachment of the antigen to the adjuvant whether by covalent or adsorption methods. Generally, the greater the crystallinity, the greater the affinity for attachment. Crystallinity can be determined by means of x-ray diffraction. In general, crystallinity can be increased by long maturation times for precipitated adjuvants, and by heating or sintering.

The inventive calcium adjuvant may be chosen independently of the active agent to be delivered to a host. In other cases, tests can be performed in order to determine an optimal antigen-adjuvant match. The adjuvant's binding capacity with the antigen in the presence of various ionic conditions and buffering agents may be screened (e.g. fluorescent labeling or radioactive labeling) and the best match is chosen. Methods for assessing binding of moieties to solid calcium phosphate in varying ionic strengths are known to the art. Efficient incorporation of the antigen or other moiety occurs when the antigen interacts strongly with the base molecule and becomes bound to it. In these cases, the antigen is most likely to remain bound to the molecule and become entrapped in the adjuvant.

The active agent may include, but is in no way limited to, antigens, vaccines, second adjuvants, bacteria or viruses, or fragments thereof, nucleic acids, proteins, heat shock proteins (HSPs), haptens, tolerogens, allergens, immunogens, antibiotics, and other bioactive moieties or components of biosynthetic pathways. A more complete listing of compounds suitable for delivery to a host can be found in *Vaccine Design, The Subunit and Adjuvant Approach* (Powell et al. (eds), Plenum Press, New York, 1995), which is incorporated herein by reference.

In some embodiments the inventive adjuvants will be used to stimulate an immune response in the absence of an active agent. For example, local implantation of an active agent-free adjuvant near a tumor may suffice to recruit a local reaction sufficient to reject the tumor. In these instances it may be advantageous to employ one or more adjuvanticity enhancers or enhancing strategies, such as the incorporation of a specific cytokine and the use of a rough surfaced vehicle. In other cases, the adjuvant is introduced to the host either before or after the antigen, but the adjuvant and the antigen are not combined as a single entity.

Dose Issues

The correct dose of immunogen to be delivered by the inventive adjuvant must be determined for each application. An absolute dose is the total amount of an active agent loaded onto the adjuvant, whereas a chronic dose is the amount of active agent released and delivered to the recipient per unit of time. The relative importance of these two aspects of dose depends on the purpose of administration and properties of the active agent. Generally, larger doses of vaccines may be required to establish immunological memory. Dosage is preferably adjusted in conjunction with the rate of adjuvant resorption: Faster resorbing adjuvants will tend to deliver dosages more quickly than a slower resorbing adjuvant because it is introduced into the host more rapidly and at an increased concentration. In preferred embodiments, the adjuvant's resorption rate will mimic a traditional initial immunization followed by subsequent or booster immunizations. The length of time between immunizations, called a rest period, is usually necessary for the induction of antigen-specific lymphocytes, particularly memory B lymphocytes, and an effective vaccination. Generally, a longer rest period (e.g. several weeks or months) will produce the maximum antibody response.

Introduction to a Host

The delivery vehicle or adjuvant is preferably introduced to a recipient as a gel or paste, but in limited cases, it may also be a solid, a slurry or a liquid. When in particulate form, the adjuvant will generally comprise particles diameters of 1 nm to 200 μm, preferably 1 nm-10 μm and most preferably 1 nm-900 nm. These particles will be either alone or present with larger particles. The delivery vehicle or adjuvant can be introduced to a host by any effective method.

In a preferred embodiment, a paste adjuvant is prepared which is injected and which hardens in the body following injection. An apatitic calcium phosphate adjuvant prepared according to example 17 can be injected subcutaneously or intramuscularly and hardens at body temperature (37° C.). The injectable paste can be introduced to a host subcutaneously, intramuscularly, intradermally or through other injection routes. In other embodiments, the adjuvant particles are mixed with a paste and injected (e.g. intramuscularly, subcutaneously, intravenously). The volume percent of particles, relative to the paste, may be adjusted depending on the desired dose or adjuvant activity. Additionally, in another embodiment, the paste may be spread like a lotion to provide transdermal, and/or mucosal delivery.

If the adjuvant is a solid, such as a pellet or block, it will generally be implanted surgically. It may also be provided as a suppository. Methods employing delivery cannula may also be employed.

In certain embodiments, the adjuvant may be suspended in a liquid or other viscous substance. In preferred embodiments, nanometer size adjuvant particles are suspended in a slurry or a liquid and administered by any appropriate means, preferably injection. The volume percent of particles in the slurry may be adjusted depending on the desired dose or adjuvant activity. In some instances, the adjuvant can be administered via peroral or ocular routes or as an inhalent (nasal administration). Administration by inhalent may employ a dry (non-hydrated) vehicle in nano or micro particulate form. Embodiments employing ocular administration of the adjuvant typically consist of drug-loaded nanoparticles suspended in a non-toxic aqueous medium and administered as an eye-drop. In some cases the particles are found in ointments and administered ocularly.

Uses-Depot Delivery and Controlled Release

The inventive adjuvant offers the advantage of either site specific delivery or systemic delivery. Once introduced to a host, the adjuvant/device will deliver the active agent. The inventive adjuvant delivers the antigen with the desired kinetics. In preferred embodiments, the adjuvant will provide a depot delivery of the antigen to the host. Additionally, the adjuvant will provide site-specific delivery of the antigen. Target site specific delivery is known to improve therapeutic efficacy of an active agent and reduce undesired side effects. Specific targets include tumor tissue, prior or subsequent sites of active agent injection and/or any site where rejection is desired or in the case of vaccination to the specific antigen preferred sites are those which lead to optimal immunization (e.g. spleen, liver, kidney, lymph nodes, etc.).

The invention is further exemplified with reference to the following examples, which are presented for the purpose of illustration only and are not to be considered as limiting of the invention.

EXAMPLES

Example 1

This example describes the preparation of an amorphous calcium phosphate (ACP) adjuvant.

Solution A was prepared at room temperature by the rapid dissolution of 55 g $Na_2HPO_4.7H_2O$; 50 g NaOH; 30 g $NaHCO_3$ in 1.3 liters of distilled water. Solution B was prepared at room temperature by rapid dissolution of 43 g $Ca(NO_3)_2.4H_2O$ in 0.5 liters of distilled water.

Carbonated amorphous calcium phosphate was then prepared at room temperature by the rapid addition of solution B to rapidly stirring solution A. The precipitate of gel-like amorphous calcium phosphate thus formed was aged or allowed to stand at room temperature for approximately 30 seconds. After aging, the precipitate was filtered using filter paper (0.05 $m^2$) with medium filter speed and a vacuum pressure of about $10^{-2}$ torr. The precipitate formed a thin cake and was washed with approximately 4 liters of distilled water by adding water into the filtrating funnel. The gel pH was measured using a pH probe and determined to be pH 13.5

Example 2

This example describes the preparation of an amorphous calcium phosphate adjuvant.

An ACP adjuvant was prepared according to example 1, but with the modification that the precipitate was aged or allowed to stand at room temperature for 5 minutes. The washed material was then collected using a spatula and immersed into a liquid nitrogen in a 2.5 L container. Following the formation of hard frozen pieces, the container was transferred into a vacuum chamber for 24 hours ($10^{-1}$-$10^{-2}$ torr), until a fine and dry powder was obtained.

Example 3

This example describes the preparation of an amorphous calcium phosphate (ACP) adjuvant.

An ACP adjuvant was prepared according to example 2, but with the modification that the precipitate was aged at room temperature for 2 hours in the presence of the mother liquid.

Example 4

This example describes the step-by-step preparation of an amorphous calcium phosphate (ACP) adjuvant.

The ACP adjuvant was prepared according to example 1 with the following modifications. Solution A was prepared at room temperature by the rapid dissolution of 80 g $Na_2HPO_4.7H_2O$; 40 g $NaHCO_3$; 1 g $Na_4P_2O_7.10H_2O$ in 1.0 liters of distilled water. Solution B was prepared at room temperature by rapid dissolution of 35 g $Ca(NO_3)_2.4H_2O$; 1 g $MgCl.6H_2O$ in 0.5 liters of distilled water.

The carbonated amorphous calcium phosphate was then prepared at room temperature by the rapid addition of solution B to rapidly stirring solution A. The precipitate of gel-like amorphous calcium phosphate thus formed was aged or allowed to stand at room temperature for approximately 30 seconds. After aging in the presence of the mother liquid, the precipitate was filtered using filter paper (0.05 $m^2$) with medium filter speed and a vacuum pressure of about $10^{-2}$ torr, The material formed a thin cake and was washed with approximately 4 liters of distilled water by adding water into the filtrating funnel. The precipitate pH was measured using a pH probe and determined to be pH 7.3.

Example 5

This example describes the preparation of an amorphous calcium phosphate (ACP) adjuvant.

The ACP adjuvant was prepared according to example 4 but with the following modification. The washed material was collected using a spatula and immersed into a liquid nitrogen in a 2.5 L container. Following freezing, the material was transferred into a vacuum chamber for 24 hours ($10^{-1}$-$10^{-2}$ torr), until a fine and dry powder was obtained.

Example 6

This example describes the preparation of an amorphous calcium phosphate (ACP) adjuvant.

The ACP adjuvant was prepared according to example 5 but with the following modification. The precipitate was aged at room temperature for 30 minutes.

Example 7

This example describes the preparation of an amorphous calcium phosphate adjuvant.

The ACP adjuvant was prepared according to example 1 but with the following modifications. Solution A was prepared at room temperature by the rapid dissolution of 55 g $Na_2HPO_4.7H_2O$; 20 g NaOH; 50 g $NaHCO_3$; 2 g $Na_2P_2O_7$ in 1.3 liters of distilled water. Solution B was prepared at room temperature by rapid dissolution of 100 g $Ca(NO_3)_2.4H_2O$; 1 g $MgCl_2.6H_2O$ in 0.7 liters of distilled water. The gel pH was measured using a pH probe and determined to be pH 9.0.

Example 8

This example describes the preparation of an amorphous calcium phosphate (ACP) adjuvant.

The ACP adjuvant was prepared according to example 7 but with the following modifications. The precipitate was aged at room temperature for 30 minutes. The washed material was then collected using a spatula and immersed into a liquid nitrogen in a 2.5 L container. Following freezing, the container was transferred into a vacuum chamber for 24 hours ($10^{-1}$-$10^{-2}$ torr), until a fine and dry powder was obtained.

Example 9

This example describes the preparation of an amorphous calcium phosphate (ACP) adjuvant.

The ACP adjuvant was prepared according to example 7 but with the modification that the precipitate was aged at room temperature for 2 hours.

Example 10

This example illustrates the typical formation of a calcium phosphate apatite adjuvant.

A solution of 218 g of disodium $Na_2HPO_4.12H_2O$) in 1.2 liters of distilled water and a solution of 70 g of $Ca(NO_3)_2.4H_2O$ in 0.5 liters of distilled water were prepared. The calcium solution was quickly poured into the phosphate solution at room temperature with stirring. Precipitation was immediate and substantially complete. The precipitate was adjusted to pH 6.4 by the addition of sodium hydroxide solution in order to avoid the formation of acidic calcium phosphates. The precipitate was aged at room temperature for 5 minutes prior to filtration. The precipitate was then filtered through a Buchner filter (with a total surface about 0.1 $m^2$), and was washed by about 3 liters of distilled water. A gel cake of low crystallinity calcium phosphate obtained on the filter paper.

Example 11

This example illustrates the typical formation of a calcium phosphate apatite adjuvant.

The calcium phosphate apatite adjuvant was prepared according to example 10 but with the following modifications. The washed precipitate was collected using a spatula and immersed into liquid nitrogen in a 2.5 L container. Following freezing, the container was transferred into a vacuum chamber for 24 hours ($10^{-1}$-$10^{-2}$ torr), until a fine and dry powder was obtained.

Example 12

This example illustrates the typical formation of a calcium phosphate apatite adjuvant.

The calcium phosphate apatite adjuvant was prepared according to example 10 except that the precipitate was adjusted to pH 7.1 by the addition of a sodium hydroxide solution.

Example 13

This example illustrates the typical formation of a calcium phosphate apatite adjuvant.

The calcium phosphate apatite adjuvant was prepared according to example 11 except that the pH of the precipitate was adjusted to pH 7.1 by titrating sodium hydroxide, and was aged at room temperature for 48 hours prior to filtration.

Example 14

This example illustrates the typical formation of a calcium phosphate apatite adjuvant.

The calcium phosphate apatite adjuvant was prepared according to example 10 but with the following modifications. The washed precipitate was then collected using a spatula and immersed into a liquid nitrogen in a 2.5 L container. Following freezing, the precipitate was transferred into a vacuum chamber for 24 hours ($10^{-1}$-$10^{-2}$ torr), until a fine and dry powder was obtained.

Example 15

This example illustrates the typical formation of a calcium phosphate apatite adjuvant.

The calcium phosphate apatite adjuvant was prepared according to example 10 but with the modifications that the pH of the precipitating solution was adjusted to pH 7.1 with the addition of sodium hydroxide prior to filtration and the precipitate was aged at room temperature for 48 hours.

Example 16

This example illustrates the preparation of an apatitic calcium phosphate adjuvant.

Dicalcium phosphate dihydrate (DCPD) was prepared at room temperature by the rapid addition of solution B (17.1 g $Ca(No_3)_2 \cdot 4H_2O$; 0.250 liters distilled water; pH 5.5-6) to a stirred solution A (10 g $H_9N_2O_4P$; 0.5 liters distilled water; pH 7.8). Immediately thereafter, the sample was filtered using filter paper (0.05 sq. m) with medium filter speed and a vacuum pressure of about $10^{-2}$ torr. The material formed a thin cake which was washed with about 2 liters of distilled water and then dried at room temperature for 24-72 hours.

Reactive amorphous calcium phosphate was prepared according to example 1. The washed material was then collected using a spatula and immersed into a liquid nitrogen in a 2.5 L container. Following freezing, the material was transferred into a vacuum chamber for 24 hours ($10^{-1}$-$10^{-2}$ torr), until a fine and dry powder was obtained. The material was then heated for 80 minutes at 455° C. (±3° C.).

The reactive amorphous calcium phosphate material was physically dry-mixed with $CaHPO_4 \cdot 2H_2O$ at 50:50 weight percent using a mortar and pestle for 3-5 minutes. Water (1 ml/g of mixed material) was then added to the powder mixture to yield a hydrated precursor of paste-like consistency. The amount of $H_2O$ added varied, depending on whether a thick or thin paste was desired. The paste material was then placed in a moist tissue environment where upon reaching body temperature (37° C.), it hardened into a solid mass. The hardening process could be delayed for several hours by placing it into a refrigerating temperature of 4° C.

Example 17

This example describes the preparation of the PCA calcium phosphate using automated mixing of the dry precursors.

Dry ACP and DCPD precursors were prepared as described in Example 16. Instead of mixing with a mortar and pestle, the ACP and DCPD were mixed using a SPEX 8510 laboratory mill with a SPEX 8505 alumna ceramic grinding chamber for 2 minutes. Preparation of the hydrated precursor was accomplished by adding from 0.7 to 1.5 mL of water per gram of mixed dry precursors.

Example 18

This example describes the local subcutaneous response in mice to a single injection in two sites of 12 test calcium-based adjuvants. These results demonstrate the ability to selectively enhance specific aspects of the cellular immune response by specific calcium phosphate adjuvants.

Saline was used as the injection control. The test adjuvants were prepared according to examples 1-8, 11-13, 15 and were then prepared as a slurry in saline and administered by subcutaneous injection, bilaterally, into the scapular/dorsal thoracic region. The dose volume was 0.05 mL for each injection site. A circle drawn with an indelible marker identified each injection site. Animals were euthanized at specific time points (72 hours, 7 days, 14 days following injection).

A partial gross pathological examination limited to both dorsal thoracic/scapular subcutaneous injection sites (left and right) and the surrounding tissues was conducted immediately on all euthanized animals. A single firm and pale raised area was noted in each of the subcutaneous injection sites (right and left) of mice from all groups dosed with the various calcium-based adjuvants euthanized at 72 hours, 7 days and 14 days post treatment. These raised areas were attributed to the subcutaneous injection of the test adjuvants.

On completion of the necropsy, the animal identification marks were retained (but not processed) in 10% neutral buffered formalin. For terminally euthanized animals, brain, spleen, thymus, right and left dorsal thoracic/scapular skin (injection sites), mandibular lymph node, liver and lung were trimmed and preserved. For each animal of the study, the right subcutaneous injection site was prepared for histopathological examination by embedding in paraffin wax, sectioning and staining with hematoxylin and eosin. The left injection site was evaluated with the following antibodies: CD3, CD4, CD8, CD45R/B220 (or alternatively CD19) and Mac-3. The right injection sites of terminal mice were directly embedded in OCT medium, frozen and stained with CD3ε, CD4 and CD8α. Left injection site of terminal mice were immediately fixed with 10% neutral buffered formalin for 6 to 24 hours followed by embedding in paraffin wax and staining with hematoxylin and eosin and CD45R/B220 and Mac-3. Tissue was cut to 6 μm sections with a cryostat for frozen tissues or rotary microtome for paraffin-embedded tissues, and stained for 60 minutes with Pharmingen monoclonal rat or hamster anti-mouse primary antibodies against Mac-3 or several CD antigens (CD3ε, CD4, CD8α and CD45R/B220).

A labeled streptavidin-biotin complex/HRP detection system (Dako No. K377) with an AEC chromogen was used to visualize the antigens. Sections were counterstained with Gill's III hematoxylin. Anti-hamster IgG (for CD3ε), goat anti-rat Ig (for CD8α, CD45R/B220 and CD4) and mouse anti-rat IgG1/IgG2a (for Mac-3) and hamster IgG isotype standard (for CD3ε), were appropriately diluted and substituted as the primary antibody on negative reagent control tissue sections in order to verify the specificity of the reaction.

The immunohistochemical staining was evaluated with a semi-quantitative technique using N (negative) and P (positive) identification protocols. A cell was considered positive when there was a cytoplasmic red fuschia staining and a cellular morphology corresponding to the cell stained with the various CDs or Mac-3 in the positive control tissues.

TABLE 1

Immunohistochemical Evaluation of Calcium Phosphate Adjuvants

| | CD3 | | | CD4 | | | CD8α | | | CD45R/B220 | | | Mac-3 | | |
|---|---|---|---|---|---|---|---|---|---|---|---|---|---|---|---|
| | 72 hr | 7 d | 14 d | 72 hr | 7 d | 14 d | 72 hr | 7 d | 14 d | 72 hr | 7 d | 14 d | 72 hr | 7 d | 14 d |
| Ex 1 | N | N | 1 | N | 1 | 1 | 1 | 1 | 1 | 1 | 4 | 4 | 3 | 2 | 3 |
| Ex 2 | N | 1 | 1 | N | 1 | 1 | N | 1 | N | 1 | 2 | 2 | 1 | 3 | 3 |
| Ex 3 | N | 1 | 1 | N | 1 | 1 | N | 1 | 1 | 1 | 2 | 3 | 1 | 3 | 4 |
| Ex 4 | N | N | N | 1 | 1 | 1 | 2 | N | N | N | 2 | 2 | 3 | 3 | 4 |
| Ex 5 | N | N | N | 1 | N | 1 | N | N | 1 | 1 | 1 | 3 | 1 | 2 | 2 |
| Ex 6 | 2 | 1 | 2 | 1 | 1 | 1 | 1 | N | 1 | N | 1 | 1 | 1 | 2 | 3 |
| Ex 7 | N | N | N | N | N | N | N | N | N | 2 | 1 | 2 | 3 | 2 | 4 |
| Ex 8 | N | 1 | 1 | N | N | 1 | N | N | N | N | N | 1 | 2 | 2 | 2 |
| Ex 11 | 1 | 1 | 1 | N | 1 | 3 | N | N | 1 | 2 | 2 | 2 | 1 | 3 | 4 |
| Ex 12 | N | N | 2 | 1 | 1 | 2 | N | 1 | 2 | N | 3 | 1 | N | 4 | 4 |
| Ex 13 | N | 1 | 1 | N | N | 1 | N | N | N | N | 2 | 2 | 3 | 3 | 4 |
| Ex 15 | N | 1 | 2 | N | 1 | 1 | N | 1 | 1 | 1 | 3 | 2 | 1 | 3 | 4 |

Key: The amount of a specific cell at the injection site was quantified using the following scoring system; N (0 cell/field/40+33, negative), 1 (1-3 cell/field/40+33, slight, few cells), 2 (4-6 cell/field/40+33, mild number of cells), 3 (9-15 cell/field/40+33 +0 moderate number of cells), 4 (>= 16 cell/field/40+33, marked number of cells). The results of this study are summarized in preceding Table 1. Cellular reaction to the adjuvant can usually be categorized into one of the following groups: strong, delayed and transient.

Key: The amount of a specific cell at the injection site was quantified using the following scoring system: N (0 cell/field/40X, negative), 1 (1-3 cell/field/40X, slight, few cells), 2 (4-8 cell/field/40X, mild number of cells), 3 (9-15 cell/field/40X, moderate number of cells), 4 (>=16 cell/field/40X, marked number of cells). The results of this study are summarized in preceding Table 1. Cellular reaction to the adjuvant can usually be categorized into one of the following groups: strong, delayed and transient.

Immunohistochemical examination: Macrophages (including the multinucleated giant cells), visualized with the Mac-3 antibody, were usually the predominant cell type at the injection site of most of the adjuvant formulation in all recovery periods. The amount of macrophages, graded as slight to marked, was seen usually with a time-related increase severity in the various groups. Examples 2, 4, 12 and 13 produced strong macrophage reaction. A delayed macrophage reaction was observed in examples 3, 6, 11 and 15. Transient macrophage reaction was seen in examples 1 and 7. Mac-3 positive cells were observed primarily adjacent to the test adjuvant and often infiltrated the peripheral region of the adjuvant. They sometimes contained intracytoplasmic material consistent with the adjuvant, possibly suggesting that Mac-3 positive cells (macrophages) were primarily involved in the resorption of the various adjuvants.

The B lymphocytes, detected with CD45R/B220 antibody, were the second most numerous type of cells seen at the injection sites. The incidence of the groups with positive B lymphocytes as well as the amount of CD45R/B220 positive cells in these groups (usually graded as slight to moderate) increased at days 7 and 14 compared to the 72 hours euthanasia time period. The lowest amount of B cells was noted at the injection site of the mice receiving adjuvants prepared according to examples 6 and 8. More specifically, the B cell reaction can be grouped as delayed, strong or transient. Example one produced a strong B cell reaction at 7 days. The adjuvants of examples 3 and 5 produced a delayed reaction. Transient B cell reaction was observed in examples 7, 12 and 15. The presence of a relatively high number of B lymphocytes at the injection sites may suggest that the mediators of the humoral immune response may play an important role in the test article-related inflammatory process.

A time-related increase incidence of the groups with positive T lymphocytes (CD3ε, CD4 and CD8α) was observed. After each euthanasia period, CD4 was the most common type of positive T cell observed in the various adjuvants. At 7 and 14 days post treatment, CD3ε was the second most commonly observed T cell. These results are reported in the following Table 2:

| | 72 hours | 7 days | 14 days |
|---|---|---|---|
| CD3ε | 2 | 6 | 9 |
| CD4 | 4 | 7 | 11 |
| CD8α | 3 | 5 | 7 |
| Total # of treated groups | 12 | 12 | 12 |

In these groups, the amount of T cells were usually graded as slight (1-3 cell/field/40X) for mice euthanized at 72 hours and 7 and 14 days post treatment. The immunohistochemical detection of these different types of T cells at the injection site. Although the number of T lymphocytes was usually lower than the number of B cells and macrophages, their presence at the injection site indicate an active local immune reaction in response to the adjuvant. An absence or lower quantity of T lymphocytes was noted in mice treated with adjuvant prepared according to examples 4, 5, 7, 8, and 13 compared with those treated with the other adjuvants. Examples 12 and 13 produced a delayed T cell reaction to CD3, while a transient T cell reaction to CD3 was observed in example 6. Examples 11 and 12 produced a delayed T cell reaction to CD4. Example 4 produced a transient T cell reaction to CD8α, while example 12 produced a delayed T cell reaction to CD8α.

In preferred embodiments, a cytokine will be combined with the adjuvant according to its action to further increase the adjuvant effect. For example, cytokines, such IFN-γ, IL-1α and IL-2β will be combined with the selective adjuvants shown to induce macrophage responses. In other cases, an adjuvant prepared according to examples 1, 3 or 5 would be combined with IL-4 or IL-13 to increase the B cell response. Additionally, such cytokines as CD27 ligand, IL-2, and IL-8 would be added to the adjuvants of examples 4, 6, 11, 12 and 15 to produce enhanced T cell reaction. Further guidance for cytokine selection can be found in Appendix II: Cytokines and their Receptors (ImmunoBiology: The Immune System in Health and Disease, Janeway-Travers, Current Biology Ltd./Garland Publishing Inc., 1996), herein incorporated by reference.

Histopathological examination: A histopathological change that could be attributed to the various types of calcium phosphate adjuvant formulations was an inflammatory cell infiltration with a fibrous capsule formation surrounding the various adjuvants. This change was observed at examined injection sites of all mice euthanized at 72 hours, 7 days and 14 days. The inflammatory cellular response was characterized by infiltration in variable proportion of mononuclear cells (including macrophages, lymphocytes and plasma cells), neutrophils, eosinophils and/or multinucleated giant cells. A slighter inflammatory cellular response and fibrous capsule formation appeared to be present at the injection site of the mice receiving the calcium phosphate adjuvants of examples 3,5,7,11, and 15 in all recovery periods compared to the mice receiving other formulations. Mononuclear inflammatory cells were always seen at the injection sites and were graded as slight to moderate. Multinucleated giant cells were primarily seen in mice euthanized at 7 and 14 days post treatment and were graded as slight to moderate. In the majority of the calcium phosphate adjuvanted groups, there was usually a time-related increased severity in the infiltration of mononuclear inflammatory cells and multinucleated giant cells, and in the fibrous capsule formation. Neutrophils and eosinophils were primarily seen in mice euthanized after 72 hours of recovery periods and were graded as slight to mild. There was a time-related decreased severity in the infiltration of eosinophils and neutrophils. The amount of adjuvant at the injection site was graded as mild to severe (or marked). There was a slight to mild decrease of adjuvant in the various treated mice euthanized on days 7 and 14 compared to those euthanized at 72 hours.

Example 19

This example shows how *Bordetella pertussis* is loaded into the adjuvant of the present invention to prepare a vaccine for whooping cough.

All solutions were prepared sterilized. The calcium adjuvant is prepared according to examples 1-16, with the following modifications. The *Bordetella pertussis* (commercially available from Pasteur Vaccins) bacilli; killed and centrifuged, are homogenized in a 0.07 M dibasic sodium phosphate sterile solution so as to obtain $4 \times 10^{10}$ bacilli per ml. The bacterial suspension of germs thus obtained is mixed with Solution A prior to mixing with Solution B. *B. pertussis* becomes absorbed to the calcium phosphate precipitate of the present invention.

Example 20

This example describes the adsorption of an active agent onto the surface of the adjuvant.

The calcium phosphate adjuvant is prepared according to examples 16 or 17. The precipitate is hardened at 37° C. The *Bordetella pertussis* (commercially available from Pasteur Vaccins) bacilli; killed and centrifuged, are homogenized in a 0.07 M dibasic sodium phosphate sterile solution so as to obtain $4 \times 10^{10}$ bacilli per ml. The adjuvant (hardened calcium phosphate precipitate) is placed (e.g. dipped) into the suspension containing the *B. pertussis* and therefore adsorbed onto the surface of the adjuvant. *B. pertussis* is allowed to adsorb onto the surface of the calcium phosphate adjuvant for at least one hour Example 21

This example illustrates the use of a calcium phosphate adjuvant with an allergen in humans.

The calcium phosphate adjuvant is prepared as a powder (particle size 10 nm to 300 nm) according to examples 1-16. House dust extract is prepared by extraction of house dust with sodium phosphate buffer and purification by ammonium sulfate precipitate. The dust extract is prepared at a concentration of 0.5 mg/ml in a saline solution and used as the hydration media. Powder is suspended to a consistency of toothpaste ($10^4$-$10^8$ poise). A 2.0 ml dose of calcium phosphate adjuvanated allergen is injected subcutaneously at the external side of the arm. Blood samples are collected before and after a course of immunotherapy, that is, at the same period with an interval of one year and an average of 13 injections. Serum samples are stored at 30° C., and total IgE concentrations and specific IgE evaluation are performed. Levels determined before and after immunotherapy are expressed in IU/ml for total IgE and as ratios of patient serum/negative reference serum for specific IgE (radiolabeling). Paired t-tests are used for the statistical evaluation of IgE levels before and after treatment. Log values are used for total IgE results so as to obtain normal distribution.

Example 22

This example illustrates the use of a calcium-based adjuvant for inactivated human immunodeficiency virus-2 (HIV-2) split whole virus as an antigen in mice.

The adjuvant was prepared according to examples 1-17. The inactivated HIV-2 split whole virus is suspended at a concentration of 0.5 mg/ml in a buffered solution and adsorbed onto the adjuvant according to the method set forth in example 20. Each mouse receives 0.5 ml of the adjuvant injected subcutaneously under the abdominal skin on day 0. The mice are killed after 10 weeks, the blood is collected and the sera is separated and individually assayed for HIV-2 antibodies. Sera is assayed by ELISA and Western blot for the presence of HIV-2 antibodies.

Example 23

This example illustrates the use of a calcium-based adjuvant for delivering a vaccine.

Keyhole-limpet hemocyanin (commercially available from Sigma®, product number: H2133 and H7017) is prepared at a concentration of 0.5 mg/ml in phosphate buffered saline pH 7.0. 0.8 ml of this solution is added to the precipitate of the amorphous calcium phosphate adjuvant of examples 1-9. IL-2 is incorporated into the ACP adjuvant according to the method of example 19. The resulting formable gel is then prepared in a ball and implanted subcutaneously in a rat. The process is repeated after four months. Blood samples are taken on a regular basis and ELISA is used to determine anti-Keyhole limpet hemocyanin antibody titers.

Example 24

This example illustrates the use of a calcium-based adjuvant with a cytokine to induce systemic antitumor immunity.

The adjuvant was prepared according to examples 1-17. Nanoparticles are prepared by use of a Retsch ZM 100 mill. Granulocyte macrophage-colony stimulating factor (GM-CSF), commercially available from PeproTech®, product number 300-03, is incorporated into the adjuvant by the adsorption method of example 19. GM-CSF-containing nanoparticles of 500 nm with irradiated B16-F10 transduced tumor cells ($4 \times 10^6$) in a ratio of 1:1 are injected subcutaneously into the left flank of mice. Two weeks later, the mice are challenged in the right flank with $10^5$ live wild-type B16 melanoma cells. Tumor growth is assessed twice weekly by palpation.

Example 25

This example demonstrates protein vaccine delivery with the use of a calcium-based adjuvant.

An amorphous calcium phosphate adjuvant is prepared according to example 1, to an average particle size of 30 nm or less, by selective sieving. Protein vaccines, diphtheria and tetanus toxoids (DPT), which can be commercially obtained from Pasteur Vaccins) are adsorbed at a concentration of 0.5 mg/mL onto the adjuvant as described in example 19. A dose of 0.5 mL of DPT-adsorbed calcium phosphate adjuvant is injected subcutaneously into a mouse. Blood samples are taken 14 days and 3 months after injection and evaluated with ELISA to determine the level of anti-diphtheria and anti-tetanus titers.

Example 26

This example demonstrates use of the calcium adjuvant of the present invention for genetic immunization. The *Plasmodium yoelii* circumsporozoite protein (PyCSP) plasmid has been shown to induce parasite-inhibitory antibodies and protective cytotoxic T cells.

The calcium adjuvant is prepared according to examples 1-17. The plasmid, PyCSP, is prepared according to the method of Mor in The Journal of Immunology (V 155, 1995, p2039). The adjuvant paste is combined by mere mixing during the hydration step with a plasmid DNA encoding the circumsporozoite protein of the malarial parasite *Plasmodium yoelii* (PyCSP). A dose of 0.5 mL of the inventive adjuvant paste, with a viscosity of $1.0 \times 10^6 - 7.0 \times 10^6$ Poise, is injected intramuscularly into mice. Serum samples are collected weekly for two months and assayed for the presence of IgM or IgG antibodies reactive with rPyCS.1 protein. At various times, mice are bled by retro-orbital puncture and the serum is stored at $-20°$ C. until assay. The mice are euthanized and their organs are removed aseptically. Single cell suspensions are prepared from the spleens, inguinal and mesenteric lymph nodes, bone marrow, and quadriceps muscles, in medium consisting of RPMI 1640 supplemented with 10% FCS. Sensitive and specific cytokine ELIspot assays are used to examine the nature of the immune response elicited.

Example 27

This example illustrates the use of the inventive calcium phosphate adjuvant used to deliver a polysaccharide vaccine to the body.

The adjuvant is prepared according to examples 1-17. Average particle size of 500 nm is selectively sieved. *Streptococcus pneumococcal* is adsorbed onto the surface of the calcium phosphate adjuvant as described in example 20. 0.5 ml of vaccine containing 50 μg each of capsular polysaccharides from Danish pneumococcal serotypes 1,2,3,4,6A, 7F, 8,9N, 12F, 14,18C, 19F, 23F, and 25 is injected subcutaneously into individual rabbits. After 3 weeks, blood samples are collected and the serum is isolated. The presence of humoral immune response or B cells is evaluated by measuring the levels of circulating *S. pneumococcal* antibodies using the Jerne hemolytic plaque assay and radioimmunoassay (RIA).

Example 28

This example illustrates the use of the adjuvant of the present invention used to deliver a killed virus or bacteria.

The adjuvant is prepared according to example 1 with selected particle size of 50 nm or less. The inactivated polio vaccine (commercially available from Pasteur Vaccins) is attached to the adjuvant according to example 19. An adjuvant dose of 0.5 mL is injected subcutaneously into a mouse. The mouse is subjected to whole polio virus 3 months later. The mouse is evaluated for survival.

Example 29

This example illustrates the use of the inventive adjuvant used to deliver a live attenuated virus.

The calcium phosphate adjuvant is prepared according to examples 16-17. Average particle size of 5 μm is selectively sieved. The vaccine is a cell-free preparation of OKA strain varicella(chickenpox)-zoster virus (VZV), available from Pasteur Vaccins. VZV is included in the hydration media at a concentration of 5.0 mg/ml. 2.0 ml paste vaccine is subcutaneously administered by injection. After 4 weeks, blood samples are taken and serum is analyzed for VZV antibodies using enzyme immunoassay (EIA), latex agglutination (LA), indirect fluorescent antibody, and fluorescent antibody membrane antigen assays.

Example 30

This example demonstrates the delivery of more than one antigen using the inventive calcium adjuvant.

calcium adjuvant was prepared according to example 1 and example 17. Commercially prepared hepatitis B vaccine (Hevac B) and diphtheria-tetanus-pertussis (DTP)-polio vaccine are available from Pasteur Vaccins. The vaccines are inactivated with formaldehyde and for the adjuvant of example 1 are combined with the adjuvant during the mixing of Solutions A and B. For the adjuvant of example 17 the vaccine is included in the hydration media at a concentration of 5.0 mg/ml. The paste is subsequently hardened at 37° C. in a humid environment, then pulverized to a particle size of 250 nm. The prepared hydrated adjuvant is injected subcutaneously. A second injection is given 6 months later and a third injection again in 6 months. Blood samples are taken the day of the first injection and each subsequent injection. HB virus seric markers (HbsAg, anti-HBs, anti-HBc) are tested for with commercial radioimmunoassays (Abbott Laboratories). Anti-toxin titers to tetanus and diphtheria are determined by the passive hemagglutination techniques using highly purified toxins that are coupled to turkey erythrocytes by glutaraldehyde. For determination of pertussis agglutinins, measurements are made using the agglutination test performed in microtiter plates.

Example 31

This example demonstrates how varying particle size effects the adjuvanticity of the present invention.

The adjuvant is prepared according to examples 1-17, but with the following modifications. The aging times of the final precipitate prior to filtration are selected to be 30 seconds, 5 minutes, 30 minutes, 2 hours, 24 hours and 48 hours. Following drying, the calcium phosphate powder is milled and sieved to average particle sizes of 10 nm, 100 nm, 250 nm, 500 nm and 900 nm and confirmed by scanning electron microscopy. Mice are injected with 2.0 ml of the calcium phosphate adjuvant either in the presence of keyhole limpet hemocyanin or without and evaluated according to example 18.

Example 32

This example illustrates an apatitic calcium phosphate adjuvant.

A poorly crystalline apatitic calcium phosphate vehicle/adjuvant is prepared according to example 16 or 17 with a density as determined by Helium pycnometry of 2.33-2.8 gm/cm$^3$ preferably 2.5 gm/cm$^3$. The bulk density is approximately 0.9-1.2 gm/cm$^3$ and the average micropore size is 85 Å. The PCA material is prepared as a paste in the presence of 0.5 mg/ml of keyhole-limpet hemocyanin hydration media. A 1 ml dose of adjuvant is injected as a paste or hardened in vitro, lyophilized, and resuspended as a paste and injected.

Example 33

This example illustrates how the immunization schedule with different adjuvant particle sizes affects the optimization of the total immunization.

Inactivated hepatitis A vaccine (available commercially from SmithKline Beecham) is prepared at a concentration of 0.5 mg/ml in a hydration media for each adjuvant particle size. Adjuvant from example 16 is hydrated with the vaccine-containing hydration medium to produce a dry paste (e.g. like modeling clay). This material is then hardened at 37 C. in 100% humidity for one hour. The hardened material is then milled and sieved and 200 nm and 750 nm particles are collected separately. A 0.5 ml immunization of each (200 nm and 750 nm) adjuvant is administered subcutaneously on a 0, 4, 8 week schedule. A second 0.5 ml immunization for each adjuvant is administered subcutaneously on a 0, 4, 24 week schedule. Blood samples are collected 24 hours after each immunization and the sera is isolated. At each time point, anti-hepatitis A antibody titers are measured using ELISA.

Example 34

This example illustrates the use of a combination of weakly and strongly resorbable calcium phosphates in one adjuvant.

Strongly resorbable calcium phosphates are prepared according to examples 16. Weakly resorbable calcium phosphate material is prepared according to example 1,2, or 3 in Ison U.S. Pat. No. 5,683,496 or example 4 or 8 in Chow U.S. Pat. No. 5,522,893. Both materials are ground separately in a SPEX 8510 laboratory mill with a SPEX 8505 alumna ceramic grinding chamber for 2 minutes. All material is sieved to collect 100 nm to 250 nm sized particles. A 1:5 mass or volume ratio of weakly and strongly resorbable particles is prepared as an injectable slurry with an appropriate amount of buffered solution containing 0.5 mg/ml of keyhole-limpet hemocyanin. The paste is stored for one hour to allow adsorption. 0.5 ml of loaded adjuvant paste is injected subcutaneously into a mouse. Blood samples are collected and sera are isolated at time-points 7 days, 14 days, and 3 months. Anti-keyhole limpet hemocyanin antibody titer level are measured using ELISA

Example 35

This example illustrates various composite formulations of a calcium phosphate adjuvant.

Calcium phosphate is prepared according to example 17. The selected active agent is prepared to a concentration at 0.5 mg/ml in hydration media such as saline and in some instances adsorbed with the supplemental material. The calcium phosphate is hydrated using the media containing the active agent. Supplemental materials are added to the hydrated calcium phosphate by mere mixing at a concentration of 0.5 mg/ml. 0.5 ml of each adjuvant paste is injected subcutaneously into mice. Table 2 represents the various formulations of the inventive adjuvant. Each formulation is evaluated according to example 18. Additionally, in those formulations involving an antigen or antigens, blood samples are taken and sera are isolated. The respective antibody titers are measured using ELISA.

TABLE 2

| | Composite formulations using inventive calcium phosphate adjuvants | | | | | | | | | | | | |
|---|---|---|---|---|---|---|---|---|---|---|---|---|---|
| | Supplemental Material (supplement: calcium phosphate adjuvant (wt/wt)) | | | | | Adjuvanticity Enhancers | | | Immunogen (0.5 mg/ml) | | Particle Size Distribution of Supplemental Material | | |
| Adjuvant | PMMA | Collagen | PLA | Sintered HA | CaSO$_4$ | GM-CSF | MDP | IL-2 | DPT | VZV | 10 nm-100 nm | 250 nm-750 nm | 750 nm-10 μm |
| A | 1:25 | | 1:10 | 1:10 | | | | | | X | 33% | 33% | 34% |
| B | | | | | | 1:25 | | | X | X | 90% | | 10% |
| C | | | | | | 1:25 | | | X | X | 10% | | 90% |
| D | | | | | 1:5 | 1:5 | | | | X | 100% | | |
| E | | | 1:1 | | 1:5 | | | | | X | | 100% | |
| F | | | | 1:10 | 1:5 | | | | | X | | | 100% |
| G | | | | | 1:5 | | | | x | x | 10% | 60% | 30% |
| H | 1:25 | | | | | 1.25 | | | | X | 50% | 50% | |
| I | | | | | | | 1:10 | x | | | | 100% | |
| J | | | | | | | 1:10 | | X | | | | 100% |
| K | | | 1:25 | | | | 1:15 | | | X | | 25% | 75% |
| L | | 1:10 | | | | | | X | | | | 64% | 36% |
| M | | | | 1:10 | | | | | | X | 100% | | |
| N | 1:25 | | | | | | | | X | | 100% | | |
| O | | | | | | 1:25 | | | | X | 100% | | |

What is claimed is:

1. A delivery composition comprising:
   a) a calcium phosphate comprising an amorphous calcium phosphate (ACP) or a poorly crystalline apatitic (PCA) calcium phosphate; and
   b) an antigen or vaccine;
   wherein said composition is formulated as an injectable paste that hardens in an endothermic reaction at body temperature to form a poorly crystalline apatitic calcium phosphate.

2. The composition of claim 1, wherein said antigen or vaccine comprises a nucleic acid molecule.

3. The composition of claim 1, wherein said delivery composition further comprises a second calcium phosphate selected from the group consisting of amorphous calcium phosphate, poorly crystalline calcium phosphate, dicalcium phosphate dihydrate, tricalcium phosphate, tetracalcium phosphate, and octacalcium phosphate.

4. A method for stimulating an immune response in a mammal, said method comprising administering the composition of claim 1, 2, or 3 to said mammal.

5. The method of claim 4, wherein said mammal is a human.

6. The method of claim 3, wherein said calcium phosphate comprises amorphous calcium phosphate and dicalcium phosphate dehydrate.

7. The composition of claim 1, wherein said composition comprises an antigen.

8. The composition of claim 1, wherein said composition comprises a vaccine.

9. The delivery composition of claim 1 further comprising a physiologically acceptable aqueous medium.

* * * * *